(12) United States Patent
Itoh et al.

(10) Patent No.: US 6,187,968 B1
(45) Date of Patent: Feb. 13, 2001

(54) PROCESS FOR THE PREPARATION OF CYCLOHEXANEDIMETHANOL

(75) Inventors: Hiroshi Itoh, Soraki-gun; Yasuhisa Yoshida, Uji; Taiichiro Iwamura, Joyo; Mikio Nakazawa, Uji, all of (JP)

(73) Assignee: SK NJC Co., Ltd., Kyungki-do (KR)

( * ) Notice: Under 35 U.S.C. 154(b), the term of this patent shall be extended for 0 days.

(21) Appl. No.: 09/202,822

(22) PCT Filed: Jun. 25, 1997

(86) PCT No.: PCT/JP97/02188

§ 371 Date: Dec. 22, 1998

§ 102(e) Date: Dec. 22, 1998

(87) PCT Pub. No.: WO98/00383

PCT Pub. Date: Jan. 8, 1998

(30) Foreign Application Priority Data

| Jun. 28, 1996 | (JP) | 8/188759 |
| Oct. 22, 1996 | (JP) | 8/359373 |
| Dec. 24, 1996 | (JP) | 8/356176 |
| Feb. 26, 1997 | (JP) | 9/059931 |

(51) Int. Cl.[7] .................................................. C07C 31/13
(52) U.S. Cl. .................................................. 568/831
(58) Field of Search .................................................. 568/831

(56) References Cited

U.S. PATENT DOCUMENTS

| 2,105,664 | * | 1/1938 | Lazier | 568/831 |
| 3,334,149 |   | 8/1967 | Akin et al. . | |
| 3,776,886 | * | 12/1973 | Schreyer | 568/831 |
| 5,286,898 |   | 2/1994 | Gustafson et al. . | |
| 5,334,779 | * | 8/1994 | Kuo | 568/831 |
| 5,387,752 |   | 2/1995 | Scarlett et al. . | |

FOREIGN PATENT DOCUMENTS

| 721329 | * | 11/1965 | (CA) | 568/831 |
| 2823165 | * | 11/1979 | (DE) . | |
| 0 656 341 A1 | | 6/1995 | (EP) . | |
| 879264 | * | 10/1961 | (GB) | 568/831 |
| 6-192146 | | 7/1994 | (JP) . | |
| 6-321823 | | 11/1994 | (JP) . | |

OTHER PUBLICATIONS

Perry, "Chemical Engineer's Handbook," 5th Ed., pp. 4–20 to 4–22, 1973.*

* cited by examiner

*Primary Examiner*—Michael L. Shippen
(74) *Attorney, Agent, or Firm*—Larson & Taylor PLC

(57) ABSTRACT

This invention provides a process for preparing cyclohexanedimethanol comprising hydrogenating a cyclohexanedicarboxylic acid dialkyl ester by a fixed-bed continuous reaction in the presence of a preformed copper-containing catalyst under the conditions of reaction temperature of 200 to 280° C., hydrogen pressure of 185 to 300 kgf/cm$^2$ and hydrogen gas feed rate of 1 to 40 cm/s in terms of superficial linear velocity, the cyclohexanedicarboxylic acid dialkyl ester being prepared, typically, by ring hydrogenating of an aromatic dicarboxylic acid dialkyl ester in the presence of a preformed supported ruthenium catalyst by a fixed-bed continuous reaction.

12 Claims, 1 Drawing Sheet

PROCESS FOR THE PREPARATION OF CYCLOHEXANEDIMETHANOL

FIELD OF THE INVENTION

Figure 1:
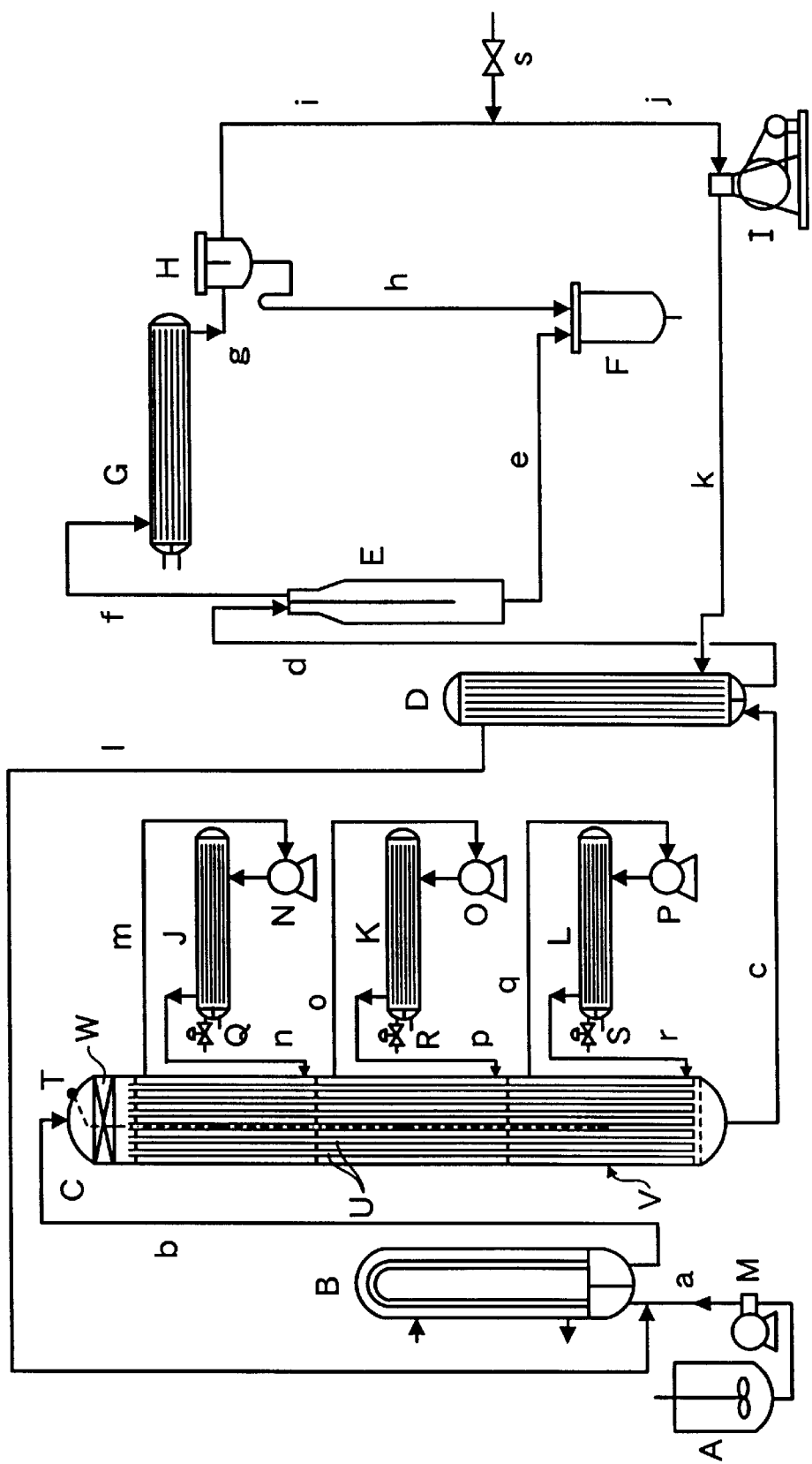

The present invention relates to a process for preparing cyclohexanedimethanol (hereinafter referred to as "CHDM"). When used as the diol component of polyester resins, polyurethane resins, polycarbonate resins or the like, CHDM is effective in improving the heat resistance, transparency, weatherability and molding properties of these resins. Particularly 1,4-cyclohexanedimethanol is drawing attention as a compound useful for improving the properties of polyethylene terephthalate.

BACKGROUND ART

Conventional processes for preparing CHDM generally comprise ring hydrogenation of aromatic dicarboxylic acid dialkyl ester to give cyclohexanedicarboxylic acid dialkyl ester (first reaction) and hydrogenation of its ester groups to give CHDM (second reaction).

Among these catalysts used for the respective reactions, known as effective for the first reaction are palladium, nickel, ruthenium, rhodium and the like (U.S. Pat. No. 3,334,149, Japanese Unexamined Patent Publications Nos. 163554/1979 and 192146/1994, U.S. Pat. No. 5,286,898 and U.S. Pat. No. 5,399,742); and known as effective for the second reaction are copper-chromite, copper oxide/zinc oxide, copper oxide/titanium oxide, copper oxide/iron oxide and catalysts prepared by modifying these copper-based catalysts with oxides of barium, magnesium and zinc and reducing the modified catalysts for activation (U.S. Pat. No. 3,334,149, Japanese Unexamined Patent Publications Nos. 192146/1994 and 196549/1995, U.S. Pat. No. 5,334,779 and U.S. Pat. No. 5,030,771, U.S. Pat. No. 4,929,777).

As the mode of reaction, a fixed-bed continuous reaction process is considered to be advantageous over a suspended catalyst reaction process in terms of productivity and yield. Herein, the fixed-bed continuous reaction process includes a reaction process (downflow-type process) wherein a pre-formed catalyst is placed into a pressure-resistant reactor, into which hydrogen and a raw material are supplied to the top of the reactor at a predetermined temperature and hydrogen pressure, and the reaction product is withdrawn from the bottom of the reactor; and a reaction process (upflow-type process) wherein hydrogen and a raw material are supplied to the bottom of the reactor and the reaction product is removed from the top of the reactor. The suspended catalyst reaction process comprises suspending a catalyst powder in an aromatic dicarboxylic acid diester or a cyclohexanedicarboxylic acid diester and subjecting the suspension to a reaction with heating while being pressurized with hydrogen.

As the examples of fixed-bed continuous reaction process, reported are processes comprising ring hydrogenation of a terephthalic acid dialkyl ester in the presence of a preformed supported ruthenium catalyst to give 1,4-cyclohexanedicarboxylic acid dialkyl ester in the first reaction (Japanese Unexamined Patent Publications Nos. 163554/1979 and 192146/1994).

Ruthenium catalysts are inexpensive compared with palladium catalysts, and exhibit a high activity even at a low pressure and a low temperature, but have the disadvantage of being likely to cause undesirable reactions involving high exothermic heat, such as hydrogenolysis of ester groups to hydroxymethyl group(s) or methyl group(s), in addition to the hydrogenation of the aromatic ring.

It is advantageous to use a cyclohexanedicarboxylic acid diester as a reaction solvent in order to avoid adverse effect due to reaction heat. However, the cyclohexanedicarboxylic acid diester used may be consumed due to the above-mentioned side reactions, not only resulting in a low yield but also, in extreme case, leading to a rapid generation of heat in a portion of the reactor which makes it difficult to continue the reaction. Therefore, Japanese Unexamined Patent Publication No. 192146/1994 proposes the provision of a perforated plate in the reactor to improve the dispersibility of gas and liquid. However, even in this case, the concentration of terephthalic acid dialkyl ester in the feed to the reactor actually must be limited to an extremely low range of 5 to 20 weight %, and a large amount of reaction product is subjected to reaction by recycling, resulting in a low yield based on the terephthalic acid dialkyl ester used and leading to a low productivity.

Examples of the fixed-bed continuous reaction process for the second reaction are those disclosed in Japanese Unexamined Patent Publications. Nos. 196549/1995; 196560/1995; 196558/1995; 196559/1995; 188077/1995; 188078/1995 and 188079/1995. These proposed processes are characterized in that the reaction is conducted under gas phase conditions of relatively low hydrogen pressure. However, the processes entail various disadvantages such as loss of thermal energy in vaporizing the raw material and necessity for removal of generated reaction heat in a gas phase of low heat conductivity, resulting in a need for complicated equipments. Furthermore, high-boiling-point by-products are deposited on the surface of catalyst, thereby markedly reducing the catalyst activity and thus necessitating frequent catalyst replacement or catalyst regeneration treatment.

On the other hand, U.S. Pat. Nos. 3,334,149, 5,030,771 and 5,334,779 and Japanese Unexamined Patent Publication No. 192146/1994 disclose a gas-liquid mixed phase reaction. However, the disclosed processes include various problems. For example, the feed rate (F/V) of cyclohexanedicarboxylic acid dialkyl ester is as low as 1/h or less, leading to a low productivity per reactor. Alternatively, cyclohexanedicarboxylic acid dialkyl ester is fed as diluted with the reaction product, i.e. CHDM or the like to a concentration of about 16% by weight or less, consequently involving complicated equipment and cumbersome operation relating to the reactor and resulting in increased by-products due to side reaction of CHDM.

DISCLOSURE OF THE INVENTION

An object of the present invention is to provide a process for preparing high-quality CHDM, which is capable of producing CHDM with safety in a high yield by a simplified procedure at a high productivity per reactor and capable of diminishing costs for equipment.

The present inventors found that in producing an alicyclic alcohol, particularly cyclohexanedimethanol, a high yield can be achieved using simplified equipment when cyclohexanedicarboxylic acid ester is hydrogenated under specific reaction conditions, and completed the present invention.

The present invention provides a process for preparing cyclohexanedimethanol represented by the formula (1)

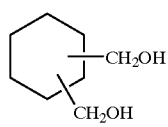

(1)

the process comprising the step of hydrogenating cyclohexanedicarboxylic acid dialkyl ester represented by the formula (2)

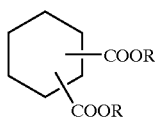

(2)

wherein R represents an alkyl group having 1 to 12 carbon atoms or a cycloalkyl group having 5 to 10 carbon atoms, and particularly represents a straight- or branched-chain alkyl group having 1 to 4 carbon atoms, by a fixed-bed continuous reaction in the presence of a preformed copper-containing catalyst under the condition of reaction temperature of 200 to 280° C., hydrogen pressure of 185 to 300 kgf/cm$^2$ and hydrogen gas feed rate of 1 to 40 cm/s in terms of superficial linear velocity.

In the specification and claims, superficial linear velocity has a generally recognized meaning and is defined as a value obtained by dividing the hydrogen gas flow rate (cm$^3$/s) by a cross-sectional area (cm$^2$) of the tubular or columnar reactor in the case of a single-column reactor, or as a value obtained by dividing the hydrogen gas flow rate (cm$^3$/s) by a total cross-sectional area (cm$^2$) of a plurality of tubes in the case of a multi-tubular reactor.

The cyclohexanedicarboxylic acid dialkyl ester of the formula (2) can advantageously be obtained by ring hydrogenation of benzenedicarboxylic acid dialkyl ester in the presence of a preformed supported ruthenium catalyst.

In the present invention, accordingly, cyclohexanedimethanol can advantageously be obtained by a process comprising the steps of hydrogenating benzenedicarboxylic acid dialkyl ester (first reaction) and hydrogenating the obtained cyclohexanedicarboxylic acid dialkyl ester in the presence of a preformed copper-containing catalyst (second reaction).

Thus, the present invention provides a process for preparing cyclohexanedimethanol represented by the formula (1)

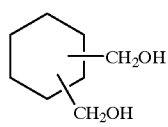

(1)

the process comprising the steps of (a) carrying out ring hydrogenation of an aromatic dicarboxylic acid dialkyl ester represented by the formula (3)

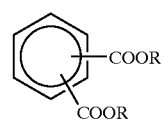

(3)

wherein R represents an alkyl group having 1 to 12 carbon atoms or a cycloalkyl group having 5 to 10 carbon atoms, and particularly represents a straight- or branched-chain alkyl group having 1 to 4 carbon atoms, in the presence of a preformed supported ruthenium catalyst by a fixed-bed continuous reaction to give cyclohexanedicarboxylic acid dialkyl ester represented by the formula (2)

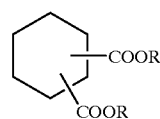

(2)

wherein R is as defined above, and (b) hydrogenating the cyclohexanedicarboxylic acid dialkyl ester obtained in step (a) and represented by the formula (2) by a fixed-bed continuous reaction in the presence of a preformed copper-containing catalyst under the conditions of reaction temperature of 200 to 280° C., hydrogen pressure of 185 to 300 kgf/cm$^2$ and hydrogen gas feed rate of 1 to 40 cm/s in terms of superficial linear velocity.

According to one embodiment of this invention (embodiment I), CHDM can be prepared by a process comprising the steps of hydrogenating the ring of a terephthalic acid dialkyl ester in the presence of a preformed supported ruthenium catalyst by a fixed-bed continuous reaction to give 1,4-cyclohexanedicarboxylic acid dialkyl ester (first reaction) and hydrogenating the obtained 1,4-cyclohexanedicarboxylic acid dialkyl ester by a fixed-bed continuous reaction in the presence of a preformed copper-chromite catalyst (second reaction) wherein the hydrogenation of the second reaction is carried out under the conditions of reaction temperature of 225 to 280° C., hydrogen pressure of 185 to 300 kgf/cm$^2$ and hydrogen gas feed rate of 1 to 40 cm/s in terms of superficial linear velocity.

This embodiment I has the feature of producing CHDM in a yield comparable to the prior art processes and furthermore extending the life of the catalyst.

According to the research of the present inventors, it has been revealed that a fixed-bed continuous reaction in a downflow-type process with use of a multitubular pressure-resistant reactor can industrially produce high-quality CHDM in high yields and at high productivity inconceivable from the prior art process.

Thus, according to another embodiment of the invention (embodiment II), there is provided a process for preparing CHDM, characterized in that it comprises the steps of hydrogenating an aromatic dicarboxylic acid dialkyl ester in the presence of a preformed supported ruthenium catalyst by a fixed-bed continuous reaction to give a corresponding cyclohexanedicarboxylic acid dialkyl ester (first reaction) and hydrogenating the obtained cyclohexanedicarboxylic acid dialkyl ester by a fixed-bed continuous reaction in the presence of a preformed copper-containing catalyst under the conditions of reaction temperature of 200 to 280° C., hydrogen pressure of 185 to 300 kgf/cm² and hydrogen gas feed rate of 1 to 40 cm/s in terms of superficial linear velocity (second reaction), wherein as the reactor for each step, a multitubular pressure-resistant reactor packed with each of the above specified catalysts is used, and wherein hydrogen and a feed composed of each raw material and if desired the reaction product and/or a solvent are fed to the top of each reactor to carry out hydrogenation under a gas-liquid mixed phase condition, and excess hydrogen and the reaction product are removed from the bottom of each reactor.

According to the research of the present inventors, it has been revealed that hydrogenation of a cyclohexanecarboxylic acid mono-, di-, tri- or tetra-alkyl ester (particularly cyclohexanedicarboxylic acid dialkyl ester) in the presence of a preformed copper-containing catalyst in substantially the same manner as in embodiment I above can produce a corresponding alicyclic alcohol (particularly CHDM), and that when the hydrogenation is carried out while feeding an aliphatic alcohol to said reaction system, high-quality CHDM can be produced by an economically advantageous process with use of a simplified equipment at high productivity.

Thus, according to a further embodiment of the invention (embodiment III), there is provided a process for preparing an alicyclic alcohol, particularly CHDM, represented by the formula (III-2)

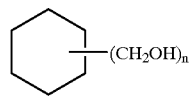

(III-2)

wherein n is as defined in the formula (III-1), the process being characterized in that it comprises the step of hydrogenating cyclohexanecarboxylic acid ester represented by the formula (III-1)

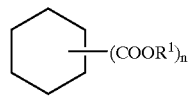

(III-1)

wherein $R^1$ is a straight- or branched-chain alkyl group having 1 to 4 carbon atoms, and n is an integer of 1 to 4, particularly 2, with the proviso that the $R^1$ groups which are n in number may be the same or different, by a fixed-bed continuous reaction in the presence of a preformed copper-containing catalyst under the conditions of reaction temperature of 200 to 280° C., hydrogen pressure of 185 to 300 kgf/cm² and hydrogen gas feed rate of 1 to 40 cm/s in terms of superficial linear velocity, wherein hydrogen, the cyclohexanecarboxylic acid ester and an aliphatic alcohol having 1 to 4 carbon atoms are fed to a reactor packed with said catalyst.

This embodiment III has the feature of improving the yield of CHDM by the use of said aliphatic alcohol even without the use of a multitubular pressure-resistant reactor described with respect to embodiment II.

According to a still further embodiment of the invention (embodiment IV), it is preferable that the cyclohexanedicarboxylic acid dialkyl ester, which is an intermediate for preparing CHDM, is prepared by a process using a ruthenium catalyst having specific physical properties. Said process is a process for preparing cyclohexanedicarboxylic acid dialkyl ester represented by the formula (IV-2)

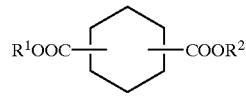

(IV-2)

wherein $R^1$ and $R^2$ are the same or different and each represents an alkyl group having 1 to 4 carbon atoms by hydrogenating an aromatic dicarboxylic acid dialkyl ester represented by the formula (IV-1)

(IV-1)

wherein $R^1$ and $R^2$ are as defined above in the presence of a preformed supported ruthenium catalyst by a fixed-bed continuous reaction, characterized in that the chlorine content of the preformed supported ruthenium catalyst is 500 ppm or less.

BRIEF DESCRIPTION DRAWING

FIG. 1 a schematic view showing the reactor used in the examples illustrating embodiment II.

DETAILED DESCRIPTION OF THE INVENTION

The above embodiments I to IV will be described below in detail.

Embodiment I

The present inventors conducted extensive research to overcome the foregoing prior art problems and found the following. In carrying out the ring hydrogenation of terephthalic acid dialkyl ester and the hydrogenation of the ester groups of 1,4-cyclohexanedicarboxylic acid dialkyl ester by a fixed-bed continuous reactor, the selection of a specific temperature range, a hydrogen pressure range and hydrogen gas feed rate, especially in the hydrogenation of the ester groups, remarkably suppresses the formation of high-boiling point by-products, consequently leading to a significantly extended life of the copper-chromite catalyst. The present invention was completed based on this finding.

Thus, the process for preparing CHDM according to embodiment I is characterized in that it comprises the steps of hydrogenating the ring of a terephthalic acid dialkyl ester in the presence of a preformed supported ruthenium catalyst by a fixed-bed continuous reaction to give 1,4-cyclohexanedicarboxylic acid dialkyl ester (first reaction) and hydrogenating the obtained 1,4-cyclohexanedicarboxylic acid dialkyl ester in the presence of a preformed copper-chromite catalyst by a fixed-bed continuous reaction to give CHDM (second reaction), wherein the hydrogenation in the second reaction is carried out under the conditions of a reaction temperature of 225 to 280° C., hydrogen pressure of 185 to 300 kgf/cm² and hydrogen feed rate of 1 to 40 cm/s in terms of superficial linear velocity.

The reactor useful for the fixed-bed continuous reaction of the present invention, for both of the first reaction and the second reaction, may be of a single column type, or of a multitubular type which comprises a plurality of tubes having a small interior diameter and arranged in parallel (shell-and-tube reactor).

First Reaction

The terephthalic acid dialkyl ester for use as the starting material is a diester prepared by esterifying terephthalic acid, as an acid component, with a straight- or branched-chain aliphatic alcohol having 1 to 12 carbon atoms or an alicyclic alcohol having 5 to 10 carbon atoms, particularly a straight- or branched-chain aliphatic alcohol having 1 to 4 carbon atoms, as an alcohol component, in the conventional manner.

While any of primary, secondary and tertiary alcohols can be used as the alcohol component, primary and secondary alcohols are preferred. Specific examples are methanol, ethanol, n-propanol, iso-propanol, n-butanol, iso-butanol, n-hexanol, cyclohexanol, n-octanol, 2-ethylhexanol, n-decanol and lauryl alcohol.

Typical examples of terephthalic acid dialkyl esters are dimethyl terephthalate, diethyl terephthalate, di-n-propyl terephthalate, di-n-butyl terephthalate and di-2-ethylhexyl terephthalate. Among them, preferred is dimethyl terephthalate which is prepared using methanol as the alcohol component and commercially available.

The preformed supported ruthenium catalyst useful in the invention can be any moldings, such as tablets, pellets, cylinders and spheres, of conventional supported ruthenium catalysts which are known as catalysts for hydrogenating aromatic rings. Examples of useful support are alumina, silica, titania, magnesia and zirconia, among which alumina is preferred.

The amount of ruthenium to be deposited on a support is recommendably 0.05 to 10% by weight, and preferably 0.1 to 5% by weight, based on the support. If the amount is less than 0.05% by weight, a pronouncedly low activity is exhibited and hence it is impractical. If the amount is more than 10% by weight, only the cost will increase without noticeably improving the catalyst activity and furthermore marked separation of the deposited ruthenium from the support takes place, hence impractical.

These preformed catalysts can be used as such, or can be used in the reaction after effecting a suitable activation treatment, such as reduction, in the conventional manner.

The shape of the preformed supported ruthenium catalyst is not specifically limited, but generally the catalysts of cylindrical shape which are commercially readily available are used. Their size can be determined according to the interior diameter of the reactor. Usually preferred are cylindrical catalysts having a diameter of 2 to 6 mm and a height of 2 to 6 mm.

In this embodiment I, it is preferable to use the specific ruthenium catalyst to be described later in embodiment IV.

Generally, the higher the hydrogen partial pressure, the more smoothly the first reaction proceeds. If the hydrogen pressure becomes higher than necessary, a special pressure-resistant reactor is required, and its use is uneconomical. Practically, it is preferable that the hydrogen pressure is in the range of 5 to 100 kgf/cm$^2$, particularly 30 to 100 kgf/cm$^2$.

Basically, the pressure in the reaction system is a sum of said hydrogen pressure and vapor pressures of the starting material and the product and partial pressures of methane gas and the like that are formed as by-products. However, the vapor pressures of the starting material and the product and partial pressures of the gas are almost negligible and therefore the reaction pressure is substantially equal to the hydrogen pressure.

The reaction temperature is, for example, in the range of 80 to 200° C., recommendably 90 to 160° C. At a reaction temperature of below 80° C., the reaction rate becomes markedly slow, whereas at a reaction temperature of above 200° C., side reactions take place preferentially, and hence impractical.

The first reaction can be conducted without use of a solvent because the starting material terephthalic acid dialkyl ester is fed as such when it is liquid, or fed as melted when it is a solid. However, a solvent is preferably used when terephthalic acid dialkyl ester used as the raw material is cumbersome to handle owing to the high melting point thereof or when it is necessary to facilitate the removal of reaction heat.

When the reaction solvent is used, the kind of the solvent is not specifically limited insofar as it does not adversely affect the reaction. Specific examples thereof include a 1,4-cyclohexanedicarboxylic acid dialkyl ester and an alcohol which correspond to the terephthalic acid dialkyl ester used as the raw material in the reaction. Particularly, the most preferred solvent is 1,4-cyclohexanedicarboxylic acid dialkyl ester.

Examples of the 1,4-cyclohexanedicarboxylic acid dialkyl ester are the reaction products obtained in the first reaction, such as dimethyl 1,4-cyclohexanedicarboxylate, diethyl 1,4-cyclohexanedicarboxylate, and dipropyl 1,4-cyclohexanedicarboxylate.

Examples of the alcohol are, for example, those corresponding to terephthalic acid dialkyl ester used as the raw material, such as methanol, ethanol, n-propanol, iso-propanol, n-butanol, iso-butanol, n-hexanol, cyclohexanol, n-octanol, 2-ethylhexanol, etc.

When the reaction solvent is used, the amount of the solvent to be used is suitably selected and is adjusted in such a manner that the concentration of terephthalic acid dialkyl ester in the system is 5 to 80% by weight, preferably 10 to 50% by weight. Below 5% by weight, a low productivity results, whereas over 80% by weight, there would be no advantage of using the solvent.

The mode of the fixed-bed hydrogenation process in the first reaction may be either of a downflow type or of an upflow type wherein the raw material and hydrogen are supplied to the top or to the bottom of the reactor packed with the above-mentioned catalyst. However, the mode of the downflow type is usually preferable from the standpoint of the catalyst life.

The feed rate of terephthalic acid dialkyl ester to be used as the raw material is preferably 0.1 to 5/h, more preferably 0.2 to 3/h, in terms of F/V (wherein F represents the feed rate (liter/h) of terephthalic acid dialkyl ester and V is the volume (liter) of the catalyst bed in the reactor.

The feed rate of hydrogen is recommendably 1 to 40 cm/s, preferably 2 to 10 cm/s, in terms of superficial linear velocity under the reaction conditions.

In this first reaction, the terephthalic acid dialkyl ester used as the raw material is substantially quantitatively hydrogenated, so that with respect to the reaction mixture discharged from the fixed-bed reactor, usually more than 95 weight % of the terephthalic acid dialkyl ester used has been converted to the desired 1,4-cyclohexanedicarboxylic acid dialkyl ester.

The thus obtained reaction mixture as such or the 1,4-cyclohexanedicarboxylic acid dialkyl ester isolated from the reaction mixture is fed, as the raw material in the second reaction, to a reactor for the second reaction. From the viewpoint of operation, it is advantageous that the reaction mixture obtained in the first reaction as such is used as the raw material of the second reaction.

Second Reaction

This embodiment I is mainly characterized in that the above reaction product of the first reaction is hydrogenated in the second reaction under the conditions of the specific reaction temperature (225–280° C.), the specific hydrogen pressure (185 to 300 kgf/cm$^2$) and the specific hydrogen gas superficial linear velocity (1 to 40 cm/s), whereby the life of the copper-chromite catalyst used is extended and the desired CHDM can be produced in a high yield.

The catalyst to be used for hydrogenation of the ester groups in the second reaction is a preformed copper-chromite catalyst. The catalyst may contain, as a promoter, oxides of barium or manganese to enhance the catalyst activity and/or to prevent the sintering of the catalyst. Further usable are those molded after addition of various binders in order to impart an improved strength to the catalyst.

Specific examples of such catalysts include, for example, commercially available preformed copper-chromite catalysts of the so-called Adkins type. Preferred are preformed multi-element type copper-chromite catalysts containing one or more promoters such as barium oxide or manganese oxide.

Generally, the copper-chromite catalyst contains copper in an amount, calculated as CuO, of 20–80 wt. %, preferably 30–70 wt. % and chromium in an amount, calculated as $Cr_2O_3$, of 15–70 wt. %, preferably 40–60 wt. %. The above Adkins type catalyst preferably contains copper in an amount, calculated as CuO, of 30–60 wt. % and chromium in an amount, calculated as $Cr_2O_3$, of 30–60 wt. %. These copper-containing catalysts preferably contain the above promoter(s) in an amount of up to 10 wt. %, calculated as the metal oxide. In this embodiment I, the content of barium or manganese is, for example, 0.5 to 10% by weight, calculated as barium oxide or manganese oxide.

In order to control exothermic heat abruptly generated at the start of the reaction and effectively exhibit a catalyst activity, it is effective that the copper-chromite catalyst is subjected to preliminary reduction treatment by conventional methods.

The shape of copper-chromite catalysts is not specifically limited, but catalysts of cylindrical shape which are commercially readily available are usually recommended. The size thereof can be determined according to the interior diameter of the reactor to be used, and usually preferred are cylindrical catalysts having a diameter of 2 to 6 mm and a height of 2 to 6 mm.

The hydrogenation conditions in the second reaction can be suitably selected depending on the kind of 1,4-cyclohexanedicarboxylic acid dialkyl ester to be used as the raw material, and are generally as follows.

The reaction temperature is in the range of 225 to 280° C., preferably 240 to 265° C. At a reaction temperature of lower than 225° C., a markedly low reaction rate is exhibited, and a high-boiling-point ester compounds are produced as by-products in a large amount, whereas at a reaction temperature of higher than 280° C., decomposition reaction and condensation reaction would markedly occur, and in either case the catalyst has a short life so that such temperature conditions are impractical. Incidentally, when a specific reactor is used as in embodiment II to be described below or when an alcohol is used as in embodiment III to be described below, reaction temperature of about 200° C. may be used.

The higher the hydrogen pressure, the more smoothly the second reaction proceeds. Practically, however, it is preferable to select the hydrogen pressure in the range of 185 to 300 kgf/cm$^2$ particularly 200 to 250 kgf/cm$^2$. At a hydrogen pressure of below 185 kgf/cm$^2$, it is difficult to achieve a suitable reaction rate and high-boiling-point ester compounds are produced as by-products in a large amount so that the catalyst life becomes short, whereas at a hydrogen pressure of above 300 kgf/cm$^2$, special pressure-resistant reactor is required, and therefore uneconomical. The pressure of the whole reaction system is basically the same as, or slightly higher than, the hydrogen pressure.

A reaction solvent is usually unnecessary, because 1,4-cyclohexanedicarboxylic acid dialkyl ester used as the raw material is usually liquid. However, a suitable solvent may be used when 1,4-cyclohexanedicarboxylic acid dialkyl ester is difficult to handle owing to the high melting point thereof or when facilitated removal of reaction heat is required.

The mode of the fixed-bed hydrogenation process in the second reaction may be either of a downflow type or of an upflow type wherein the raw material and hydrogen are supplied to the top or the bottom of the reactor packed with the above preformed catalysts. However, the mode of the downflow type is usually preferable from the standpoint of the catalyst life.

The feed rate of 1,4-cyclohexanedicarboxylic acid dialkyl ester is recommendably 0.1 to 5/h, preferably 0.2 to 2/h, in terms of F/V (wherein F represents the feed rate (liter/h) of 1,4-cyclohexanedicarboxylic acid dialkyl ester and V is the volume (liter) of the catalyst bed in the reactor.

The feed rate of hydrogen is recommendably 1 to 40 cm/s, preferably 2 to 20 cm/s, in terms of superficial linear velocity under the reaction conditions. At a superficial linear velocity of lower than 1 cm/s, the reaction rate decreases and the quantity of by-products increases. On the other hand, at a feed rate of higher than 40 cm/s, there is no further appreciable improvement in the reaction rate, resulting in economical disadvantage, and the duration of activity and catalyst strength would decrease.

In this reaction, the ester groups of the 1,4-cyclohexanedicarboxylic acid dialkyl ester used as the raw material are substantially quantitatively converted to hydroxymethyl group by hydrogenation, so that the reaction mixture discharged from the fixed-bed reactor usually contains the desired 1,4-cyclohexanedimethanol in an amount of more than 95% by weight based on the weight of the reaction mixture excluding the formed alcohol and also excluding the solvent(s) when the solvent(s) is(are) used.

The thus-obtained CHDM can be purified by conventional methods such as distillation.

Embodiment II

According to embodiment II of the present invention, there is provided a process characterized in that the process comprises the steps of:

(a) hydrogenating an aromatic dicarboxylic acid dialkyl ester with use of a preformed supported ruthenium catalyst by a fixed-bed continuous reaction to give a corresponding cyclohexanedicarboxylic acid dialkyl ester (first reaction), and (b) hydrogenating the obtained cyclohaxanedicarboxylic acid dialkyl ester by a fixed-bed continuous reaction in the presence of a preformed copper-containing catalyst under the conditions of reaction temperature of 200 to 280° C., hydrogen pressure of 185 to 300 kgf/cm$^2$ and hydrogen gas feed rate of 1 to 40 cm/s in terms of superficial linear velocity to prepare cyclohexanedimethanol (second reaction), wherein a multitubular pressure-resistant reactor packed with each of the above specified catalysts is used as the reactor in each of the steps (a) and (b), and wherein hydrogen and each raw material are fed to the top of each reactor to effect hydrogenation under a gas-liquid mixed phase condition, and excess hydrogen and the reaction product are withdrawn from the bottom of each reactor.

In other words, according to said embodiment II of the invention, there is provided a process for preparing cyclohexanedimethanol, the process comprising the steps of:

(a) continuously feeding an aromatic dicarboxylic acid dialkyl ester and hydrogen to the top of a multitubular pressure-resistant reactor packed with a preformed supported ruthenium catalyst to effect hydrogenation under a gas-liquid mixed phase condition, and removing excess hydrogen and the corresponding cyclohexanedicarboxylic acid dialkyl ester from the bottom of said reactor (first reaction), and (b) continuously feeding the cyclohexanedicarboxylic acid dialkyl ester obtained in step (a) above and hydrogen to the top of a multitubular pressure-resistant reactor packed with a preformed copper-containing catalyst to effect hydrogenation under a gas-liquid mixed phase condition and under the conditions of reaction temperature of 200 to 280° C., hydrogen pressure of 185 to 300 kgf/cm$^2$ and hydrogen gas feed rate of 1 to 40 cm/s in terms of superficial linear velocity, and removing excess hydrogen and the resulting cyclohexanedimethanol from the bottom of said reactor (second reaction).

Desirably the following conditions are employed in embodiment II.

In the first reaction, namely in step (a), it is preferable that the hydrogen pressure is 30 to 100 kgf/cm$^2$, the reaction temperature is 120 to 180° C., the superficial linear velocity of hydrogen gas is 1 to 15 cm/s, particularly 1 to 10 cm/s, and the concentration of the aromatic dicarboxylic acid dialkyl ester in the feed to the reactor is at least 30% by weight.

In the second reaction, namely step (b), it is preferable that the hydrogen pressure is 185 to 300 kgf/cm$^2$, the reaction temperature is 200 to 280° C., the superficial linear velocity of hydrogen gas is 1 to 40 cm/s, more preferably 5 to 30 cm/s, and the concentration of cyclohexanedicarboxylic acid dialkyl ester in the feed to the reactor is at least 90% by weight.

In the second reaction, cyclohexanedicarboxylic acid dialkyl ester is preferably fed at a feed rate (F/V) of 1.1 to 3.0/h (F/V=feed rate per hour relative to the volume of the catalyst bed in the reactor; F is a feed rate (liter/h) of the cyclohexanedicarboxylic acid dialkyl ester and V is a volume (liter) of the catalyst bed in the reactor).

Further, the reactor to be used in embodiment II preferably comprises a shell and a plurality of tubes arranged in parallel and housed in the shell, and a heat transfer medium is passed through the shell to heat or cool the tubes. Especially, it is preferable that the shell for the reactor for the first reaction is divided into at least two zones, and that the temperature of each of the zones can be independently controlled, whereby the temperature difference within the reactor will be not greater than 50 degrees (° C.), particularly not greater than 30 degrees (° C.).

Preferably the reactor for step (a), namely the first reaction is heated or cooled with a shell having at least two zones, and the heat transfer media flowing through the zones are independently heated or cooled so that the temperature difference in the reactor will be not greater than 50 degrees (° C.).

The reactors to be used for the fixed-bed continuous reaction according to embodiment II, for both of the first and second reactions, are multitubular reactors, in which a plurality of tubes having a small interior diameter are arranged in parallel, and which are equipped with means for heating and cooling a heat transfer medium flowing through a shell thereof.

The interior diameter of each tube constituting the multitubular reactor is preferably 2.5 to 10 cm, in particular 3 to 6 cm. If tubes each having an interior diameter of less than 2.5 cm are used, the number of tubes required for achieving the desired production output will be excessive and additionally the productivity will be lowered. Conversely, if tubes each having an interior diameter of larger than 10 cm are used, the gas-liquid dispersion efficiency is lowered, making it difficult to achieve the high productivity, high quality and high yield as contemplated in the present invention.

Preferably, each tube has a length of 3 to 15 m, particularly 5 to 10 m. The use of tubes less than 3 m or over 15 m in length results in pronouncedly reduced productivity and lowered yield of the desired CHDM.

The number of tubes is advantageously at least 10, particularly 10 to 2000, in view of the cost for manufacturing the reactor. However, it should be noted that the upper limit of the number of tubes is not particularly restricted but may be suitably selected depending on the desired production output.

The shell through which the heat transfer medium passes may be of a non-partition type or of a multi-partition type internally separated into plural zones, the temperature each of which can be independently controlled. Especially, the reactor for the first reaction preferably has a shell of a multi-partition type with at least 2 zones, preferably 3 to 6 zones. If the first reaction is conducted under a temperature control in a single-zone cell, there is a tendency that an intensive exothermic reaction can not be controlled, causing various side reactions and resulting in a low-quality product and a diminished yield.

As the mode of the fixed-bed continuous reaction according to embodiment II, a gas-liquid mixed phase downflow-type process is carried out, wherein hydrogen gas and raw material are fed to the top of the reactor packed with the preformed catalyst, and the reaction product and the excess hydrogen are removed from the bottom of the reactor, and wherein the reaction is carried out under the reaction temperature and hydrogen feed rate conditions such that the reaction temperature is lower than the dew point of at least one of the raw material and the product.

Problems are raised if the reaction of embodiment II is conducted by an upflow-type process wherein a raw material and hydrogen are fed from the bottom of the reactor or by a countercurrent-type process wherein, for example, raw material is fed to the top of the reactor and hydrogen is supplied to the bottom of the reactor. In such case, the strength of catalyst is adversely affected by the friction caused due to the movement of the catalysts, necessitating frequent replacement of catalysts. Especially, ruthenium metal is separated from the catalyst used in the first reaction and is lost, whereby the activity of the catalyst is reduced within a short period of time.

Also, under the gas phase conditions in which the reaction temperature is above a dew points of the raw material and the reaction product, high-boiling-point by-products are deposited on the surface of catalyst, significantly reducing the catalyst activity, thereby necessitating frequent replacement of catalysts and regeneration treatment thereof. Furthermore, under such conditions, it is necessary to remove the reaction heat in a gas phase of low heat conductivity so that extremely complicated equipment is required.

First Reaction

In the first reaction according to embodiment II, an aromatic dicarboxylic acid dialkyl ester is hydrogenated in the presence of a preformed supported ruthenium catalyst to give the corresponding cyclohexanedicarboxylic dialkyl ester.

The aromatic dicarboxylic acid dialkyl ester to be used as the raw material is a diester prepared by esterifying terephthalic acid, isophthalic acid or phthalic acid with a monohydric aliphatic alcohol having 1 to 4 carbon atoms in the conventional manner. Among these diesters, preferred is a compound represented by the formula (II-1)

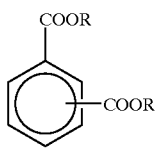

(II-1)

wherein R is an alkyl group having 1 to 4 carbon atoms.

Specific examples of the above alcohol ROH are methanol, ethanol, n-propanol, iso-propanol, n-butanol, iso-butanol, etc.

Thus, examples of the aromatic dicarboxylic acid dialkyl ester are dimethyl terephthalate, diethyl terephthalate, di-iso-propyl terephthalate, di-n-butyl terephthalate, dimethyl isophthalate, diethyl isophthalate, di-iso-propyl isophthalate, di-n-butyl isophthalate, dimethyl phthalate, diethyl phthalate, di-iso-propyl phthalate, di-n-butyl phthalate, etc. Among them, the most preferred are commercially available dimethyl terephthalate and dimethyl isophthalate prepared from methanol.

Useful preformed supported ruthenium catalyst include conventional preformed supported ruthenium catalysts which are known as catalysts for hydrogenating aromatic rings.

Useful carriers or support can be any of alumina, silica, titania, magnesia, zirconia, silicon carbide and the like, among which alumina is preferred.

The amount of ruthenium to be deposited on the support is preferably 0.05 to 10% by weight, more preferably 0.1 to 5% by weight, based on the support.

As to the shape of the preformed supported ruthenium catalyst, generally recommended are those of cylindrical shape which are commercially readily available.

The size of the preformed catalyst can be determined according to the interior diameter of the reactor to be used. Usually preferred are cylindrical catalysts having a diameter of 2 to 6 mm and a height of 2 to 6 mm.

These preformed catalysts can be used as such or can be subjected to the reaction after being suitably activated as by reduction.

The specific ruthenium catalyst to be described later in embodiment IV may be used in this embodiment II as well.

Generally, the higher the hydrogen partial pressure, the more smoothly the hydrogenation reaction proceeds. If the hydrogen pressure is higher than necessary, a special pressure-resistant reactor is required, and hence uneconomical.

The pressure to be employed in the first reaction is preferably in the range of 30 to 100 kgf/cm². At a pressure of below 30 kgf/cm², a low reaction rate results, hence undesirable. Above 100 kgf/cm², in addition to the above-mentioned equipment problem, various disadvantages result. For example, side reactions which involve large amount of exothermic heat tend to occur, such as hydrogenolysis of ester groups to hydroxymethyl group(s) or to methyl group(s). Further, low yields and difficulty in the control of reaction are entailed.

A preferred reaction temperature is in the range of 120 to 180° C. At a reaction temperature of below 120° C., a reaction rate is markedly low, whereas at a reaction temperature of above 180° C., side reactions preferentially occur. Hence the reaction temperature outside said range is not practical.

The first reaction is preferably carried out utilizing the above-mentioned mode of heating or cooling the heat transfer medium to maintain a temperature difference within 50 degrees (° C.), preferably within 30 degrees (° C.), in the longitudinal direction of tube within the reactor (namely in the direction of fluid flow). If there is a temperature difference beyond this range in the tubes of the reactor, there take place side reactions involving high exothermic heat, such as hydrogenolysis of ester groups to hydroxymethyl group(s) or to methyl group(s), which tend to induce lowered yield and markedly decreased productivity.

The aromatic dicarboxylic acid dialkyl ester can be continuously fed to the top of the reactor either singly or in the form of a mixture with the reaction product obtained in the first reaction and mainly containing cyclohexanedicarboxylic acid dialkyl ester. In the latter case, high-melting-point aromatic dicarboxylic acid dialkyl ester becomes easily melted and the reaction heat is easily controlled.

As to the proportions of the aromatic dicarboxylic acid dialkyl ester and the first reaction's reaction product, since the above-mentioned multitubular reactor is used, the higher the concentration of the aromatic dicarboxylic acid dialkyl ester is, the more preferable from the standpoint of productivity and suppression of the formation of by-products. Accordingly, it is recommendable that the concentration of the aromatic dicarboxylic acid dialkyl ester in the mixture is at least 30% by weight, more preferably at least 40% by weight.

At a low concentration of less than 30% by weight, a low productivity results, and the side reaction of cyclohexanedicarboxylic acid dialkyl ester circulating through the reaction system takes place, causing the decrease in yield and selectivity. The aromatic dicarboxylic acid dialkyl ester can be used as diluted with a solvent other than the product of the first reaction, which solvent will not adversely affect the reaction. The use of such solvent, however, requires additional procedures for separating and recovering the solvent and does not give a particularly favorable result.

Recommended feed rate of the aromatic dicarboxylic acid dialkyl ester is 0.1 to 5/h, preferably 0.2 to 3/h, and particularly preferable feed rate is 0.5 to 3/h, in terms of F/V (=feed rate of the aromatic dicarboxylic acid dialkyl ester per hour relative to the volume of the catalyst bed in the reactor). At a feed rate of lower than this range, productivity is lower, whereas at a feed rate of higher than this range, the resulting reaction product contains a large amount of unreacted aromatic dicarboxylic acid ester and is not suitable as the raw material in the second reaction. Herein, F stands for the feed rate (liter/h) of the aromatic dicarboxylic acid dialkyl ester per hour, and V represents the volume (liter) of catalyst bed in the reactor.

The feed rate of hydrogen is 1 to 15 cm/s, preferably 1 to 10 cm/s in terms of superficial linear velocity under the reaction condition. At a superficial linear velocity lower than this range, it is difficult to achieve an effective contact between the gas and liquid on the surface of the catalyst with the result that the reaction rate is decreased and the quantity of by-products due to the above-mentioned side reactions increases. On the other hand, at a feed rate higher than the above range, there is no further appreciable improvement in the reaction, resulting in economical disadvantage. Hence it is undesirable.

Second Reaction

The second reaction according to embodiment II is a reaction to hydrogenate the hydrogenation product of the aromatic dicarboxylic acid dialkyl ester of the formula (II-1) obtained in the first reaction, namely cyclohexanedicarboxylic acid dialkyl ester, using a preformed copper-containing catalyst to give a corresponding CHDM.

Examples of useful preformed copper-containing catalysts include conventional preformed copper-containing catalysts having ability to reduce esters, such as copper-chromite, copper oxide/zinc oxide, copper oxide/iron oxide, copper oxide/aluminum oxide, and these catalysts which contain oxide(s) of barium, manganese, aluminum, zinc or magnesium as a promoter.

Further usable are those molded after addition of various binders in order to maintain an improved strength of the catalyst, and supported catalysts prepared by depositing said oxides on a support such as alumina, silica, silica-alumina, silicon carbide, zirconia, titania or zinc oxide.

Among the above copper-containing catalysts, particularly preferred are commercially available copper-chromite catalysts of the so-called Adkins type, copper oxide/zinc oxide catalysts and these catalysts which contain one or more promoters such as barium oxide or manganese oxide.

Generally, the above copper-containing catalysts contain copper in an amount, calculated as CuO, of 20–80 wt. %, preferably 30–70 wt. % and chromium in an amount, calculated as $Cr_2O_3$, of 15–70 wt. %, preferably 40–60 wt. %. The above Adkins type catalyst preferably contains copper in an amount, calculated as CuO, of 30–60 wt. % and chromium in an amount, calculated as $Cr_2O_3$, of 30–60 wt. %. Other copper/metal oxide catalysts mentioned above preferably contains copper in an amount, calculated as CuO, of 20–95 wt. % and other metal in an amount, calculated as the metal oxide, of 5–80 wt. %. These copper-containing catalysts preferably contain said one or more promoters mentioned above in an amount of up to 10 wt. %, calculated as said metal oxide. In the case of the supported catalysts, the percentage values are those calculated after excluding the amount of the support.

In order to control an exothermic heat abruptly generated at the start of reaction and effectively exhibit a catalyst activity, it is effective that the preformed copper-containing catalyst is subjected to preliminary reduction treatment.

The preliminary reduction treatment can be conducted in a conventional manner under a stream of hydrogen-nitrogen gas mixture at an atmospheric pressure or elevated pressure at a temperature in the range of 150 to 300° C. while gradually increasing the concentration of hydrogen.

As to the shape of copper-containing catalysts, catalysts of cylindrical shape which are commercially readily available are usually recommended.

The size thereof can be determined according to the interior diameter of the reactor to be used, and usually preferred are cylindrical catalysts having a diameter of 2 to 6 mm and a height of 2 to 6 mm.

The hydrogen pressure is preferably 185 to 300 $kgf/cm^2$, more preferably 200 to 250 $kgf/cm^2$. If the hydrogen pressure is below this range, various disadvantages are entailed, in addition to reduced reaction rate and decreased productivity, including increase in the quantity of high-boiling-point by-products such as ether compounds and wax esters and lowered yields and selectivity. A lower hydrogen pressure is also undesirable from the viewpoint of the duration of catalytic acitivity and strength of the catalyst. Conversely, the use of a hydrogen pressure of greater than the above range only increases the equipment cost without further appreciable improvement in the reaction rate and selectivity, hence undesirable.

The reaction temperature is preferably 200 to 280° C., more preferably 225 to 280° C. At a reaction temperature of below this temperature range, a markedly low reaction rate is exhibited, whereas at a reaction temperature higher than the above range, side reactions predominantly occur. Hence the reaction temperature outside said range tends to be impractical.

In the second reaction, usually the reaction product obtained in the first reaction is continuously supplied, as it is, to the top of the reactor. The amount of unreacted aromatic dicarboxylic acid dialkyl ester in the reaction product obtained by the first reaction is preferably controlled to 5% by weight or less for producing the desired CHDM in a high yield.

Also a portion of the reaction product obtained in the second reaction and predominantly containing CHDM may be fed as mixed with the reaction product obtained in the first reaction, but the concentration of cyclohexanedicarboxylic acid dialkyl ester in such feed to the second reaction reactor is preferably at least 90% by weight in view of the productivity and the increase in the amount of by-products due to relatively prolonged exposure of the desired CHDM to the reaction environment.

The feed rate of the reaction product obtained in the first reaction and to be fed to the reactor for the second reaction is preferably 1.1 to 3.0/h, in terms of F/V based on cyclohexanedicarboxylic acid dialkyl ester. If the F/V value is less than 1.1/h, productivity is low with economical disadvantage, and also the yield of the desired CHDM is reduced due to side reactions, hence undesirable. Conversely, at a feed rate in excess of 3.0/h, the obtained reaction product contains unreacted cyclohexanedicarboxylic acid dialkyl ester which brings about pronounced decrease in the yield and purity.

Recommended feed rate of hydrogen gas is 1 to 40 cm/s, preferably 5 to 30 cm/s, particularly 10 to 20 cm/s, in terms of superficial linear velocity. The hydrogen gas superficial linear velocity has an extremely remarkable effect on the second reaction, and at a velocity of less than 5 cm/s, particularly less than 1 cm/s, the reaction rate significantly reduces, making it difficult to achieve the high productivity as contemplated in the present invention. On the other hand, at a superficial linear velocity of more than 30 cm/s, particularly more than 40 cm/s, a further advantage in terms of the reaction is not achieved, and the duration of activity and strength of the catalyst decreases, and only the costs for equipment such as a hydrogen circulator and for energy increases, hence undesirable.

Embodiment III

According to the present inventors' research, it has been found that when cyclohexane mono-, di-, tri- or tetra-carboxylic acid lower alkyl ester is used as the raw material, together with an aliphatic alcohol having 1 to 4 carbon atoms, in the same manner as in the second reaction according to embodiment I, the corresponding alicyclic alcohol, i.e. cyclohexane-mono-, di-, tri or tetramethanol can be produced.

Thus, according to embodiment III of the present invention, there is provided a process for preparing an alicyclic alcohol, particularly cyclohexanedimethanol (CHDM), represented by the formula (III-2)

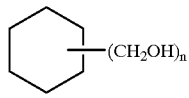
(III-2)

wherein n is as defined in the formula (III-I), the process comprising the steps of hydrogenating a cyclohexanecarboxylic acid ester represented by the formula (III-1)

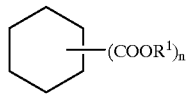
(III-1)

wherein $R^1$ is a straight- or branched-chain alkyl group having 1 to 4 carbon atoms, and n is an integer of 1 to 4, particularly 2 provided that the $R^1$ groups which are n in number may be the same or different, in the presence of a preformed copper-containing catalyst by a fixed-bed continuous reaction, wherein hydrogen, the cyclohexanecarboxylic acid ester of the formula (III-1) and aliphatic alcohol having 1 to 4 carbon atoms are fed to a reactor packed with said catalyst.

In embodiment III, preferably hydrogen, a cyclohexanecarboxylic acid ester of the formula (III-1) and an aliphatic alcohol having 1 to 4 carbon atoms are fed to the top of the reactor packed with said preformed copper-containing catalyst, and excess hydrogen, the reaction product of the formula (III-2) and the aliphatic alcohol having 1 to 4 carbon atoms are removed from the bottom of the reactor.

A preferred amount of the aliphatic alcohol having 1 to 4 carbon atoms to be fed to the reaction system is 1 to 100% by weight based on the ester used as the raw material.

Desirably the cyclohexanecarboxylic acid ester represented by the formula (III-1) is cyclohexanedicarboxylic acid diester and the alicyclic alcohol represented by the formula (III-2) is cyclohexanedimethanol.

According to embodiment III, the alicyclic alcohol is prepared, for example, by the following process.

The reaction apparatus used is equipped with a preheater for hydrogen, a preheater for the raw materials, a reactor having a shell for heating or cooling by a heat transfer medium, a gas-liquid separator and a hydrogen gas circulator. First, a predetermined amount of a preformed copper-containing catalyst is placed into the reactor, and the catalyst is activated in the conventional manner. Then predetermined amounts of a cyclohexanecarboxylic acid ester and an aliphatic alcohol having 1 to 4 carbon atoms are fed, along with hydrogen gas, to the reactor from its top while maintaining the reaction system at a specific hydrogen pressure, a specific temperature and a specific superficial linear velocity of hydrogen gas.

The multitubular reactor described with respect to embodiment II is preferably used, but according to embodiment III wherein the above-mentioned specific alcohol is used, a conventional reactor of the short single-tube type having a shorter tube length and larger tube diameter may also be used.

Examples of the cyclohexanecarboxylic acid ester of the formula (III-1) useful as the raw material include an aromatic ring hydrogenation product of an ester prepared by esterifying benzoic acid, terephthalic acid, isophthalic acid, phthalic acid, trimellitic acid, trimesic acid, pyromellitic acid or the like with an aliphatic alcohol having 1 to 4 carbon atoms in the conventional manner.

When plural carboxyl groups are attached to the cyclohexane ring of cyclohexanecarboxylic acid ester, steric configuration thereof may be R- or S-isomer or a mixture of R- and S-isomers.

Specific examples of cyclohexanecarboxylic acid esters of the formula (III-1) are products obtained by hydrogenating the aromatic ring of esters such as methyl benzoate, ethyl benzoate, n-propyl benzoate, iso-propyl benzoate, n-butyl benzoate, iso-butyl benzoate, dimethyl terephthalate, diethyl terephthalate, di-n-propyl terephthalate, di-iso-propyl terephthalate, di-n-butyl terephthalate, di-iso-butyl terephthalate, dimethyl isophthalate, diethyl isophthalate, di-n-propyl isophthalate, di-iso-propyl isophthalate, di-n-butyl isophthalate, di-iso-butyl isophthalate, dimethyl phthalate, diethyl phthalate, di-n-propyl phthalate, di-iso-propyl phthalate, di-n-butyl phthalate, di-iso-butyl phthalate, trimethyl trimellitate, triethyl trimellitate, tri-n-propyl trimellitate, tri-iso-propyl trimellitate, tri-n-butyl trimellitate, tri-iso-butyl trimellitate, trimethyl trimesate, triethyl trimesate, tri-n-propyl trimesate, tri-iso-propyl trimesate, tri-n-butyl trimesate, tri-iso-butyl trimesate, tetramethyl pyromellitate, tetraethyl pyromellitate, tetra-n-propyl pyromellitate, tetra-iso-propyl pyromellitate, tetra-n-butyl pyromellitate, tetra-iso-butyl pyromellitate, etc.

Further it is possible to use cyclohexanecarboxylic acid esters having mixed ester groups such as methyl ethyl terephthalate, methyl butyl phthalate, ethyl butyl isophthalate, etc.

Among said cyclohexanecarboxylic acid esters, preferred are commercially available methyl esters prepared from methanol, and the most preferred are dimethyl 1,4-cyclohexanedicarboxylate and dimethyl 1,3-cyclohexanedicarboxylate which are aromatic ring hydrogenation products of dimethyl terephthalate and dimethyl isophthalate.

Methods of hydrogenating the aromatic ring are not specifically limited and include conventional methods such as a method comprising hydrogenating aromatic carboxylic acid ester in the presence of a preformed supported ruthenium catalyst at a hydrogen pressure of 5 to 100 kgf/cm$^2$ and at a reaction temperature of about 80 to about 200° C.

The cyclohexanecarboxylic acid ester of the formula (III-1) can also be prepared by esterifying in the conventional manner cyclohexanecarboxylic acid prepared separately with an aliphatic alcohol having 1 to 4 carbon atoms.

Usable as the catalyst for hydrogenation of ester group or groups are conventional preformed copper-containing catalysts capable of reducing esters. Specific examples are copper-chromite, copper oxide/zinc oxide, copper oxide/iron oxide, and these catalysts which contain, as a promoter, oxides of barium, manganese, aluminum, zinc or magnesium. Useful catalysts further include preformed catalysts molded after addition of various binders to maintain the strength of catalyst, and supported catalysts prepared by depositing said oxide on a support such as alumina, silica, silica-alumina, silicon carbide, zirconia, titania or zinc oxide.

Among said copper-containing catalysts, preferred are commercially available copper-chromite catalysts of the so-called Adkins type, preformed copper oxide/zinc oxide catalysts, and these catalysts which contain barium oxide, manganese oxide or the like as a promoter.

Generally, the above copper-chromite catalysts contain copper in an amount, calculated as CuO, of 20–80 wt. %, preferably 30–70 wt. % and chromium in an amount, calculated as $Cr_2O_3$, of 15–70 wt. %, preferably 40–60 wt. %. The above Adkins type catalyst preferably contains copper in an amount, calculated as CuO, of 30–60 wt. % and chromium in an amount, calculated as $Cr_2O_3$, of 30–60 wt. %. Other copper/metal oxide catalysts mentioned above preferably contains copper in an amount, calculated as CuO, of 20–95 wt. % and other metal in an amount, calculated as the metal oxide, of 5–80 wt. %. These copper-containing catalyst preferably contain one or more promoters mentioned above in an amount of up to 10 wt. %, calculated as said metal oxide. In the case of the supported catalysts, the percentage values are those calculated after excluding the amount of the support.

The shape of the preformed copper-containing catalyst is not specifically limited, and usually preferred are catalysts of cylindrical shape that are commercially readily available. The size of the preformed catalyst can be determined according to the interior diameter of the reactor to be used. Usually preferred are cylindrical catalysts having a diameter of 2 to 6 mm and a height of 2 to 6 mm.

In order to control exothermic heat abruptly generated at the start of reaction or to effectively exhibit a catalyst activity, it is effective that the preformed copper-containing catalyst may be subjected to preliminary reduction treatment.

The preliminary reduction treatment can be conducted in the conventional manner under a stream of hydrogen-nitrogen gas mixture at an atmospheric pressure or elevated pressure and a temperature of 150 to 300° C. while gradually increasing the concentration of hydrogen.

Recommended hydrogenation temperature is 200 to 280° C., particularly 200 to 270° C., more preferably 220 to 250° C. Below 200° C., the ester used as the raw material is hydrogenated to an insufficient degree, whereas above 280° C., hydrogenolysis occurs, so that the temperature in either case is undesirable.

A recommendable hydrogen pressure is 185 to 300 kgf/$cm^2$, preferably 200 to 250 kgf/$cm^2$. At a hydrogen pressure of below this range, various disadvantages are entailed and include not only reduced reaction rate and decreased productivity, but also increased quantities of high-boiling-point by-products such as ether compounds and wax esters, and lowered yields and selectivity. A lower hydrogen pressure is undesirable also from the viewpoint of duration of activity and strength of the catalyst. Conversely, a hydrogen pressure of above this range, only the equipment cost increases without appreciably enhancing the reaction rate and selectivity, hence undesirable.

Recommended feed rate of hydrogen is 1 to 40 cm/s, particularly 5 to 30 cm/s, and particularly preferable feed rate is 10 to 20 cm/s, in terms of superficial linear velocity. The superficial linear velocity of hydrogen gas has an extremely marked effect. At less than 1 cm/s, reaction rate is significantly low, making it difficult to achieve the high productivity as contemplated in the present invention. A velocity of above 40 cm/s does not provide a further advantage in terms of the reaction, only resulting in increased costs for equipment such as a hydrogen circulator and for energy, hence undesirable.

A preferred feed rate of the ester to be used as the raw material is 1.1 to 3.0/h in terms of F/V based on cyclohexanecarboxylic acid ester. If the F/V value is below 1.1/h, productivity is decreased, giving an economical disadvantage and the desired alcohol is produced in a lower yield due to side reactions, whereas if the feed rate is above 3.0 /h, the obtained reaction product contains unreacted cyclohexanecarboxylic acid ester, and decreased yield and purity result. Herein, F stands for the feed rate (liter/h) for feeding the cyclohexanecarboxylic acid ester per hour, and V represents the volume (liter) of catalyst bed in the reactor.

Useful lower aliphatic alcohols to be fed to the reaction system include, for example, $C_{1-4}$ straight-chain or $C_{3-4}$ branched-chain aliphatic alcohols such as methanol, ethanol, n-propanol, iso-propanol, n-butanol, iso-butanol, etc. Considering the procedure during the recovery treatment, it is favorable that these alcohols be the same as the alcohol component ($R^1OH$) constituting the cyclohexanecarboxylic acid ester of the formula (III-1) used as the raw material.

Generally, the hydrogenation of cyclohexane-carboxylic acid ester can be represented by the following formula (III-3)

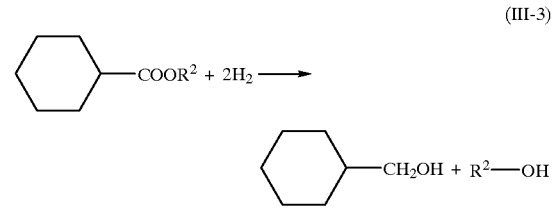

(III-3)

wherein $R^2$ is a straight- or branched-chain alkyl group having 1 to 4 carbon atoms.

However, as the hydrogenation reaction proceeds and the product alicyclic alcohol becomes in excess, an ester interchange reaction occurs between the cyclohexanecarboxylic acid ester and the produced alicyclic alcohol to achieve an equilibrium relation of the formula (III-4). It is considered that generally a lower alkyl ester is hydrogenated faster than an alicyclic alkyl ester which is shown in the right side of the formula (III-4).

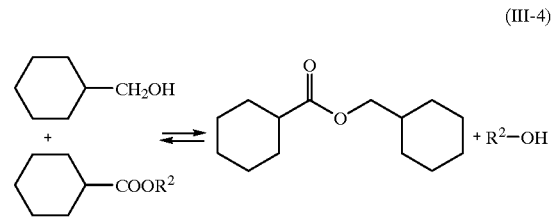

(III-4)

Consequently, if a lower aliphatic alcohol which is the same as the constituent of the ester used as the raw material is added to the reaction system, the equilibrium relation is considered to move toward the starting cyclohexanecarboxylic acid lower alkyl ester side, to thereby promote the hydrogenation reaction. The present invention is based on said mechanism as the background.

The amount of aliphatic alcohol to be fed is preferably 1 to 100% by weight, more preferably 10 to 80% by weight, based on the ester of the formula (III-1) used as the raw material. If the amount is less than 1% by weight, it is difficult to obtain the contemplated result, whereas if the alcohol is fed in an amount in excess of 100% by weight, it is difficult to achieve further remarkably improved effect.

The reaction vessel for the hydrogenation reaction is not specifically limited, and even a single column type reactor can be used. A multitubular reactor can also be used which comprises a plurality of tubes having a small interior diameter and arranged in parallel.

As the mode of hydrogenation reaction, there may be mentioned a mode comprising feeding hydrogen and raw material ester and aliphatic alcohol to the top or to the bottom of a fixed-bed reactor. However, when hydrogen, a raw material and an alcohol are fed from the bottom of the reactor, there arise problems such as decrease in duration of activity and strength of the catalyst due to the use of the lower aliphatic alcohol. Accordingly hydrogen, an ester and aliphatic alcohol as the raw materials are preferably fed to the top of the reactor to undergo a reaction by the downflow-type process.

When hydrogenation is conducted under said conditions, an alicyclic alcohol can be produced in a high yield. Further, the reaction product can be purified by conventional methods such as distillation.

Embodiment IV

According to the present inventors' research, it has been found that when a chlorine content of the ruthenium catalyst used for hydrogenating an aromatic dicarboxylic acid dialkyl ester to produce cyclohexane-dicarboxylic acid dialkyl ester is 500 ppm or less, the desired cyclohexanedicarboxylic acid dialkyl ester is advantageously produced.

Therefore, the desired CHDM is advantageously prepared by using this method in the first reaction of the foregoing embodiment I and embodiment II.

Thus, according to the embodiment IV, the cyclohexanedicarboxylic acid dialkyl ester which is an intermediate for preparing CHDM is particularly prepared by a process for preparing cyclohexanedicarboxylic acid dialkyl ester represented by the formula (IV-2)

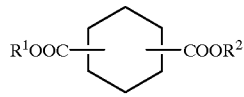

(IV-2)

wherein $R^1$ and $R^2$ are the same or different and each represents an alkyl group having 1 to 4 carbon atoms, the process being characterized in that it comprises the step of hydrogenating an aromatic dicarboxylic acid dialkyl ester represented by the formula (IV-1)

(IV-1)

wherein $R^1$ and $R^2$ are as defined above in the presence of a preformed supported ruthenium catalyst by a fixed-bed continuous reaction, wherein the preformed supported ruthenium catalyst has a chlorine content of 500 ppm or less.

Conventional processes for preparing cyclohexanedicarboxylic acid dialkyl ester include a process comprising carrying out ring hydrogenation of an aromatic dicarboxylic acid dialkyl ester. A typical example of such processes comprises ring hydrogenation of a terephthalic acid dialkyl ester in the presence of a preformed supported ruthenium catalyst by a fixed-bed continuous process to give 1,4-cyclohexanedicarboxylic acid dialkyl ester (Japanese Unexamined Patent Publications Nos. 163554/1979 and 192146/1994).

Ruthenium catalysts are inexpensive compared with palladium catalysts and exhibit a high activity at a low pressure and a low temperature, but have the drawback of being likely to cause not only the hydrogenation of aromatic ring but side reactions involving high exothermic heat, such as hydrogenolysis of ester groups to hydroxymethyl group(s) or to methyl group(s).

Japanese Unexamined Patent Publication No. 163554/1979 discloses a technique using lithium alumina as a support in an attempt to improve the duration of the catalyst activity. However, the disclosed technique remains to be improved because low productivity is entailed when an aromatic dicarboxylic acid dialkyl ester is used as the raw material.

In the process disclosed in Japanese Unexamined Patent Publication No. 192146/1994, hydrogenation is feasible under relatively mild conditions. However, the concentration of terephthalic acid dialkyl ester in the feed to the reactor is as low as 5 to 20% by weight, and a large amount of reaction product is subjected to the reaction by recycling, resulting in a low yield based on the terephthalic acid dialkyl ester used and leading to a reduced productivity.

In hydrogenating an aromatic dicarboxylic acid dialkyl ester by a fixed-bed continuous process using a preformed supported ruthenium catalyst, this embodiment IV contemplates to provide a novel and useful process for preparing cyclohexanedicarboxylic acid dialkyl ester with safety at a high productivity on a commercial scale using less complicated production facilities without a likelihood of evolution of heat owing to side reactions even when the raw material aromatic dicarboxylic acid dialkyl ester is used at a high concentration.

The present inventors conducted extensive research to overcome the foregoing problems and found that when a preformed supported ruthenium catalyst having specific characteristics is used in ring hydrogenation of said ester, the desired effect can be achieved. Based on this finding, the present invention relating to embodiment IV was completed.

The aromatic dicarboxylic acid dialkyl ester to be used in embodiment IV is a dialkyl ester prepared by esterifying terephthalic acid, isophthalic acid or phthalic acid with a monohydric aliphatic alcohol having 1 to 4 carbon atoms in the conventional manner.

Specific examples of the monohydric aliphatic alcohol to be used are methanol, ethanol, n-propanol, iso-propanol, n-butanol, iso-butanol, etc.

Specific examples of the aromatic dicarboxylic acid dialkyl ester to be used are dimethyl terephthalate, diethyl terephthalate, di-iso-propyl terephthalate, di-iso-butyl terephthalate, dimethyl isophthalate, diethyl isophthalate, di-iso-propyl isophthalate, di-iso-butyl isophthalate, dimethyl phthalate, diethyl phthalate, di-iso-propyl phthalate, di-iso-butyl phthalate, etc. Among them, preferred are commercially readily available dimethyl terephthalate, dimethyl isophthalate and/or dimethyl phthalate which are prepared from methanol.

The preformed supported ruthenium catalyst to be used in embodiment IV has a chlorine content in the preformed supported catalyst in a proportion of up to 500 ppm, preferably 50 to 300 ppm. By adjusting the chlorine content within the above range, reactions other than the ring hydrogenation reaction, namely side reactions, particularly hydrogenolysis reaction involving cleavage of carbon-oxygen bonds, is advantageously suppressed so that hydroxymethylcyclohexanecarboxylic acid alkyl ester and methylcyclohexanecarboxylic acid alkyl ester are produced as by-products in decreased amounts, resulting in a improved yield of the desired cyclohexanedicarboxylic acid dialkyl ester.

Such supported ruthenium catalysts are readily prepared, for example, by depositing ruthenium chloride ($RuCl_3 \cdot 3H_2O$) on a support in a conventional manner, sufficiently neutralizing the supported catalyst with an alkali and washing the neutralized catalyst with water until the chlorine content becomes up to 500 ppm, followed by drying and reduction.

Among the preformed supported ruthenium catalysts with a chlorine content of up to 500 ppm, preferable are those having dispersion of ruthenium, surface distribution thereof and/or pore volume thereof that fall within specific ranges. That is, preferred catalysts are those which fulfil at least one of the following requirements (i), (ii) and (iii).

(i) having a dispersion of ruthenium of at least 15%, preferably at least 20%. The preformed supported ruthenium catalyst which is at least 15% in the dispersion of ruthenium exhibits a high catalyst activity and achieves high reaction selectivity. The term "dispersion of ruthenium" used herein refers to the percentage of the ruthenium atoms exposed on the surface of the catalyst, relative to all the atoms of ruthenium deposited on a support.

(ii) being at least 80 wt. %, preferably at least 90 wt. %, in the surface distribution of ruthenium. If a catalyst is at least 80 wt. % in the surface distribution of ruthenium, the catalyst has a high effectivity of the ruthenium metal on the surface of a support and exhibit an improved catalyst activity, hence more advantageous in practical use. The term "surface distribution of ruthenium" is used herein to mean the percentage (weight %) of the ruthenium located no deeper than 200 μm from the external surface of the support relative to the total amount of ruthenium.

(iii) being at least 0.20 cc/g, preferably 0.25 to 0.35 cc/g, in the pore volume. If the catalyst has a pore volume of at least 0.20 cc/g, the catalyst is excellent in catalyst activity and in duration of activity. Hence such catalyst is improved in practical use. Herein, the pore volume is determined by the mercury intrusion porosimetry.

In short, particularly recommendable preformed supported ruthenium catalysts are those which are not higher than 500 ppm in chlorine content, at least 15% in dispersion of ruthenium, at least 80% by weight in surface distribution of ruthenium and at least 0.20 cc/g in pore volume.

A preferred amount of ruthenium to be deposited on a support is 0.05 to 10% by weight, based on the support. If the amount is less than 0.05% by weight, the catalyst activity is low, hence the catalyst is unsuitable for use. If the amount is more than 10% by weight, it is difficult to impart a high dispersion of ruthenium, and results in low effectivity of expensive ruthenium and markedly low reaction selectivity.

Useful support can be alumina, silica, titania, magnesia, zirconia, silicon carbide and the like, among which alumina is preferred.

As to the shape of the preformed supported ruthenium catalyst, recommended are catalysts of cylindrical shape which are commercially readily available. The size of the preformed catalyst can be suitably selected according to the interior diameter of the fixed-bed reactor to be used. Usually preferred are preformed catalysts in the form of cylinders having a diameter of 2 to 6 mm and a height of 2 to 6 mm.

These preformed supported ruthenium catalysts can be used as such, or can be used in the reaction after effecting a suitable activation treatment, such as reduction, in the conventional manner.

As to the recommended mode of the fixed-bed hydrogenation reaction according to the present invention, there may be mentioned a gas-liquid mixed phase downflow-type process. The gas-liquid mixed phase downflow-type process is a process which comprises feeding hydrogen gas and a liquid feed (a melt of raw material or a mixture of a raw material and a solvent) to the top of a fixed bed reactor packed with the above-mentioned preformed catalyst, and removing the reaction product and excess hydrogen from the bottom of the reactor, wherein the reaction is carried out under the reaction temperature and hydrogen flow rate conditions such that the reaction temperature is lower than the dew point of at least one of the raw material and the product.

Problems are raised if the fixed-bed continuous reaction is conducted by an upflow-type process (wherein the raw material and hydrogen are fed from the bottom of the reactor) or by a countercurrent-type process (wherein, for example, the raw material is fed from the top of the reactor and hydrogen is supplied from the bottom of the reactor). In such case, the strength of catalyst is adversely affected by the friction caused by the movement of the catalysts, necessitating frequent replacement of catalysts. Furthermore, ruthenium metal is separated from the preformed supported ruthenium catalyst and is lost, whereby the activity of the catalyst is reduced within a short period of time.

Also, in the reaction mode wherein the reaction is carried out at a reaction temperature which is higher than the dew points of the raw materials and the reaction product (gas phase reaction mode), high-boiling-point by-products are deposited on the surface of the catalyst, significantly reducing the catalyst activity, thereby necessitating frequent replacement of the catalyst and regeneration treatment thereof. Furthermore, under such conditions, it is necessary to remove the reaction heat in a gas phase of low heat conductivity so that complicated equipment is required.

From a commercial viewpoint, it is more preferable to feed to the reactor a raw material (which is normally solid) after conversion to a liquid form by using a solvent, than to feed the raw materials after melting it by heating.

Solvents useful for this purpose include, for example, the cyclohexanedicarboxylic acid dialkyl ester produced as the reaction product according to the invention, recommendably cyclohexanedicarboxylic acid dialkyl ester corresponding to the aromatic dicarboxylic acid dialkyl ester used as the raw material.

Preferred proportions of aromatic dicarboxylic acid dialkyl ester and cyclohexanedicarboxylic acid dialkyl ester to be used in this case are such that the concentration of the former is at least 5% by weight, particularly at least 30% by weight, more preferably at least 40% by weight. At a low concentration of less than 30% by weight, particularly less than 5% by weight, a low productivity results, and the yield and selectivity tend to decrease due to side reaction of cyclohexanedicarboxylic acid dialkyl ester circulating through the reaction system.

Among useful solvents other than cyclohexanedicarboxylic acid dialkyl ester, the alcohol component constituting the aromatic dicarboxylic acid dialkyl ester, i.e. the above-mentioned monohydric aliphatic alcohol, is usable but necessitates the separation and recovery of the solvent without gaining a particularly good result.

Recommendable feed rate of the aromatic dicarboxylic acid dialkyl ester to be used as the raw material is 0.1 to 5/h, particularly 0.2 to 3/h, and particularly preferable feed rate is 0.5 to 3/h, in terms of F/V (feed rate per hour relative to the volume of the catalyst bed in the reactor). If it is fed at a feed rate of below said range, the reaction achieves lower productivity and is impractical, whereas if it is fed at a feed rate exceeding said range, the resulting reaction product contains a large amount of unreacted aromatic dicarboxylic acid dialkyl ester, resulting in significantly low yield and purity, hence undesirable.

The feed rate of hydrogen is preferably 1 to 40 cm/s, particularly 1 to 10 cm/s, in terms of superficial linear velocity. In the case of linear velocity less than 1 cm/s, an effective contact between the gas and liquid can not be achieved on the surface of the catalyst, and the reaction rate decreases and the quantities of by-products of side reactions increases. On the other hand, at a linear velocity higher than 40 cm/s, no further improvement in the reaction is observed, resulting in economical disadvantage, hence undesirable.

Generally, the higher the hydrogen partial pressure is, the more smoothly the hydrogenation reaction proceeds. Yet, if the hydrogen pressure is higher than necessary, a special pressure-resistant reactor is required, hence economically disadvantageous. Therefore, preferred hydrogen pressure is in the range of 30 to 100 kgf/cm$^2$. The use of a hydrogen pressure of less than 30 kgf/cm$^2$ results in a low reaction rate and is undesirable. Above 100 kgf/cm$^2$, in addition to the above-mentioned equipment problem, various disadvantages result. For example side reactions which involve large amount of exothermic heat tend to occur, such as reduction of ester groups or hydrogenolysis of ester groups to methyl group(s). Further, low yields and difficulty in the control of reaction are entailed.

The reaction crude solution discharged along with excess hydrogen gas from the fixed-bed reactor is cooled and separated from the hydrogen gas by a high-pressure gas liquid separator, followed by recovery.

The recovered reaction crude solution is purified by distillation when so required.

Examples

The following are examples of the embodiments I to IV which illustrate the present invention in further detail. In the following Examples and Comparative Examples, the term "L" means "liter".

First, examples of embodiment I are described.

Example I-1

[First Reaction]

A fixed-bed reactor (20 mm in inner diameter, 1 m in length and 0.314 L in volume) was charged with 360 g of tableted catalyst (3.2 mm in diameter and 3.2 mm in height) comprising 0.5 wt. % of Ru supported on alumina.

A solution consisting of 30 wt. % of dimethyl terephthalate and 70 wt. % of dimethyl 1,4-cyclohexanedicarboxylate was fed to the top of the reactor at a rate of 628 ml/h (F/V=0.6/h), together with 1.3 Nm$^3$/h of hydrogen gas (superficial linear velocity under the reaction conditions=4 cm/s), to continuously carry out ring hydrogenation under the conditions of 140° C. and 40 kg/cm$^2$G.

After carrying out the above fixed-bed continuous ring hydrogenation for 10 hours, the the obtained crude reaction product was analyzed by gas chromatography. The composition of the product was as follows.

| | |
|---|---|
| Dimethyl 1,4-cyclohexanedicarboxylate | 96.5 wt. % |
| Low-boiling-point product | 2.4 wt. % |

-continued

| | |
|---|---|
| Methyl 4-hydroxymethylcyclohexane-carboxylate | 0.8 wt. % |
| Dimethyl terephthalate | 0.2 wt. % |
| High-boiling-point product | 0.1 wt. % |

[Second Reaction]

A fixed-bed reactor (20 mm in inner diameter, 1 m in length and 0.314 L in volume) was charged with 490 g of a tableted copper-chromite catalyst (3.5 mm in diameter and 3.5 mm in height) containing barium and manganese (47 wt. % of copper oxide, 48 wt. % of chromium oxide, 2.5 wt. % of barium oxide and 2.5 wt. % of manganese oxide). The catalyst was then subjected to preliminary activation treatment with use of a hydrogen-nitrogen mixed gas.

After the preliminary activation treatment, the crude product of ring hydrogenation in the first reaction was fed to the top of the reactor at a rate of 251 ml/h (F/V=0.8/h) at a temperature of 230° C. and a pressure of 200 kg/cm$^2$G, together with 4.9 Nm$^3$/h of hydrogen gas (superficial linear velocity under the reaction conditions=4 cm/s), to continuously carry out hydrogenation of ester groups.

The crude reaction product obtained by carrying out hydrogenation of the ester groups by the above fixed-bed continuous hydrogenation for 10 hours, 1.5 months and 3 months were analyzed for the composition thereof by gas chromatography. The results are shown in Table 1.

Example I-2

The hydrogenation of the ester groups was continuously carried out in the same manner as in the second reaction in Example I-1 except that the crude reaction product of the ring hydrogenation was fed at a rate of 377 ml/h (F/V=1.2/h) at a reaction temperature of 260° C. The results obtained are shown in Table 1.

Comparative Example I-1

The second reaction in Example I-1 was repeated with the exception that hydrogenation of the ring hydrogenation product was carried out at a pressure of 150 kg/cm$^2$G. The results of the reaction are shown in Table 1.

Comparative Example I-2

The second reaction in Example I-1 was repeated with the exception that the hydrogenation of the ring hydrogenation product was carried out at a temperature of 215° C. The results of the reaction are shown in Table 1.

TABLE 1

| | Example | | Comp. Example | |
|---|---|---|---|---|
| | I-1 | I-2 | I-1 | I-2 |
| Low boiling-point product | | | | |
| in 10 hours | 2.0 | 2.0 | 1.8 | 0.8 |
| in 1.5 months | 2.1 | 2.1 | 1.7 | 1.7 |
| in 3 months | 2.1 | 2.1 | — | — |
| HDMT 1) | | | | |
| in 10 hours | 0.9 | 0.2 | 1.4 | 2.4 |
| in 1.5 months | 1.4 | 0.4 | 2.4 | 3.4 |
| in 3 months | 1.5 | 0.5 | — | — |

TABLE 1-continued

|  | Example | | (wt. %) Comp. Example | |
|---|---|---|---|---|
|  | I-1 | I-2 | I-1 | I-2 |
| MOL 2) | | | | |
| in 10 hours | 1.2 | 2.2 | 5.0 | 5.7 |
| in 1.5 months | 1.3 | 2.3 | 7.2 | 7.2 |
| in 3 months | 1.4 | 2.4 | — | — |
| CHDM | | | | |
| in 10 hours | 95.9 | 95.6 | 89.6 | 85.9 |
| in 1.5 months | 95.2 | 95.2 | 84.2 | 81.2 |
| in 3 months | 95.0 | 95.0 | — | — |
| High boiling-point product | | | | |
| in 10 hours | trace | trace | 2.2 | 5.2 |
| in 1.5 months | trace | trace | 4.5 | 6.5 |
| in 3 months | trace | trace | — | — |

Note: 1) HDMT: Dimethyl 1,4-cyclohexanedicarboxylate
2) MOL: Methyl 4-hydroxymethylcyclohexane-carboxylate According to embodiment I of the present invention, the copper-chromite catalyst used in the second reaction is remarkably improved in duration of the catalyst activity, and the desired 1,4-cyclohexanedimethanol can be produced in a high yield with high productivity on a commercial scale.

Hereinafter, the present invention will be described in detail with reference to the following examples of embodiment II.

[Reactor]

The reactor used in the following examples is a multitubular pressure-resistant vessel comprising 15 pressure-resistant tubes U each having an inner diameter of 43 mm and a length of 5 m, and a shell V for heating or cooling the tubes by means of a heat transfer medium is divided into three zones, wherein the temperature each of the zones are independently controllable. The raw material and hydrogen fed to the top of the reactor are evenly distributed among the tubes via a distributor W provided in a chamber at the top of the reactor. While monitoring the temperature with multi-point thermometers set in the tubes, the reaction temperature was maintained within the desired range by controlling the temperature of the heat transfer medium in each of the zones. The catalyst was uniformly packed into the tubes in such a manner that the total volume of the catalyst bed was 100 L. FIG. 1 shows a schematic view of the reactor.

The symbols in FIG. 1 designate the following.
A Raw material tank
B Preheater
C Multitubular reactor
D Heat exchanger
E Gas-liquid separator
F Crude reaction product tank
G Hydrogen gas condenser
H Mist separator
I Hydrogen gas circulator
J–L Heat transfer medium heating/cooling units
M Raw material feed pump
N–P Heat transfer medium circulation pumps
Q–S Cooling medium control valves
T Multi-point thermometer
U Tube
V Shell (for heat transfer medium)
W Distributor
a–s Conduits Referring to FIG. 1, the reaction will be schematically described.

The raw material is pumped from a raw material tank A to a preheater B, together with hydrogen, by means of a raw material feed pump M through a conduit a. The heated raw material and hydrogen are fed to the top of the reactor C through a conduit b.

The crude reaction product and excess hydrogen are conveyed from the bottom of the reactor through a conduit c to a heat exchanger D where they are subjected to heat exchange with circulating hydrogen, and conveyed to a gas-liquid separator E through a conduit d. The liquid separated in this separator enters into a crude reaction product tank F through a conduit e. The gas separated in the separator E passes through a conduit f into a condenser G for cooling, and is conveyed through a conduit g to a mist separator H where the condensate is separated.

The condensate enters into the tank F through a conduit h. The hydrogen gas from the mist separator H passes through conduits i and j into a hydrogen gas circulator I, and is conveyed to the heat exchanger D through a conduit k. The hydrogen gas heated in the heat exchanger D enters into the preheater B through a conduit l. The hydrogen gas is pressurized and fed through a conduit s to a conduit j.

The heat transfer medium shell is divided into three zones. In the first zone at the upper part of the reactor, the heat transfer medium flowing out from the upper part of the first zone passes through a conduit m and is pumped to a heat transfer medium heating/cooling unit J by means of a heat transfer medium circulation pump N. The heat transfer medium cooled or heated in the unit J is fed through a conduit n to the lower part of the first zone and circulated. Similarly, in the second and third zones, the heat transfer medium drawn from the upper part thereof is pumped by means of a heat transfer medium circulation pump O or P to, and heated or cooled in, a heating/cooling unit K or L, fed to the lower part of each zone and circulated.

In the following examples, crude liquid product of ring hydrogenation reaction (product of the first reaction) was prepared in the first reaction and stocked in an amount specified. Then, in the second reaction step, said crude liquid product of the ring hydrogenation reaction was placed in raw material tank A, and the catalyst used in the first reaction was replaced by the catalyst (copper-chromite catalyst or the like) to be used in the second reaction in the multitubular reactor C, and the second reaction was carried out.

However, it is commercially advantageous to carry out the first reaction and second reaction in a continuous manner using a reactor for the first reaction containing the ruthenium catalyst and a reactor for the second reaction containing the copper-chromite catalyst or the like.

[Composition Analysis]

The compositions of the raw materials and products of the first and second reactions in the examples were analyzed by gas chromatography.

Example II-1

[First Reaction]

The reactor was charged with 95 kg of a tableted catalyst (3.2 mm in diameter and 3.2 mm in height) comprising 1.0 wt. % of Ru supported on alumina. To the top of the reactor, a solution consisting of:

| | |
|---|---|
| Dimethyl terephthalate | 50.0 wt. % |
| Dimethyl 1,4-cyclohexanedicarboxylate | 48.9 wt. % |
| Methyl 4-hydroxymethylcyclohexane carboxylate | 0.3 wt. % |
| Methyl 4-methylcyclohexanecarboxylate | 0.8 wt. % | was fed at a rate of 300 L/h(F/V=1.5/h), together with 207 Nm$^3$/h of hydrogen gas (superficial linear velocity under the reaction conditions =5 cm/s), to continuously carry out ring hydrogenation at a pressure of 80 kgf/cm². The reaction temperature was adjusted to 144 to 150° C. in the upper part of the reactor, 143 to 147° C. in the middle art of the reactor and 139 to 144° C. in the lower part of the reactor. The maximum temperature difference in the reactor was 11° C.

The composition of the crude liquid reaction product obtained by the above fixed-bed continuous ring hydrogenation reaction during the period between 5 hours and 15 hours after the start of the reaction is shown below.

| | |
|---|---|
| Dimethyl 1,4-cyclohexanedicarboxylate | 97.9 wt. % |
| Methyl 4-hydroxymethylcyclohexane carboxylate | 0.6 wt. % |
| Methyl 4-methylcyclohexanecarboxylate | 1.4 wt. % |
| Dimethyl terephthalate | 0.1 wt. % |

[Second Reaction]

The reactor was packed with 155 kg of tableted copper-chromite catalyst (3.5 mm in diameter and 3.5 mm in length) containing barium and manganese (47 wt. % of copper oxide, 48 wt. % of chromium oxide, 2.5 wt. % of barium oxide and 2.5 wt. % of manganese oxide). The catalyst was then subjected to preliminary activation treatment in a stream of hydrogen-nitrogen mixed gas at atmospheric pressure at a temperature of 180 to 200° C., while gradually increasing the hydrogen concentration.

After the preliminary activation treatment, the crude liquid reaction product of ring hydrogenation obtained in the first reaction was fed to the top of the reactor at a feed rate of 188 L/h(F/V=1.84/h) at a pressure of 250 kgf/cm², together with 2135 Nm³/h of hydrogen gas (superficial linear velocity under the reaction conditions=20 cm/s), to continuously carry out hydrogenation of the ester groups. The reaction temperature was independently adjusted to 232 to 235° C. in the upper part of the reactor, 230 to 236° C. in the middle part of the reactor and 228 to 232° C. in the lower part of the reactor.

The reaction product obtained by the above fixed-bed continuous hydrogenation of the ester groups during the period between 5 hours and 10 hours after the start of the reaction was of the following composition.

| | |
|---|---|
| 1,4-Cyclohexanedimethanol | 97.9 wt. % |
| Dimethyl 1,4-cyclohexanedicarboxylate | 0.0 wt. % |
| Methyl 4-hydroxymethylcyclohexane-carboxylate | 0.0 wt. % |
| Low-boiling-point product | 2.1 wt. % |
| High-boiling-point product | Trace |

Example II-2

[First Reaction]

The reactor was charged with 93 kg of a tableted catalyst (3.2 mm in diameter and 3.2 mm in height) comprising 0.5 wt. % of Ru supported on alumina. Dimethyl terephthalate was fed to the top of the reactor at a rate of 80 L/h(F/V= 0.8/h), together with 170 Nm³/h of hydrogen gas (superficial linear velocity under the reaction conditions=8 cm/s), to continuously carry out ring hydrogenation at a pressure of 40 kgf/cm². The reaction temperature was independently adjusted to 146 to 152° C. in the upper part of the reactor, 138 to 142° C. in the middle part of the reactor and 128 to 132° C. in the lower part of the reactor. The maximum temperature difference in the reactor was 20° C.

The crude liquid reaction product obtained by the above fixed-bed continuous ring hydrogenation reaction during the period between 5 hours and 10 hours after the start of the reaction was of the following composition.

| | |
|---|---|
| Dimethyl 1,4-cyclohexanedicarboxylate | 97.6 wt. % |
| Methyl 4-hydroxymethylcyclohexane carboxylate | 0.5 wt. % |
| Methyl 4-methylcyclohexanecarboxylate | 1.9 wt. % |
| Dimethyl terephthalate | 0.0 wt. % |

[Second Reaction]

Following the procedure of the second reaction in Example II-1, the crude liquid product of the above first reaction was fed to the top of the reactor at a rate of 120 L/h (F/V=1.17/h) at a pressure of 200 kgf/cm², together with 855 Nm³/h of hydrogen gas (superficial linear velocity under the reaction conditions=10 cm/s), to continuously carry out hydrogenation of ester groups. The reaction temperature was adjusted to 232 to 235° C. in the upper part of the reactor, 230 to 236° C. in the middle part of the reactor and 228 to 232° C. in the lower part of the reactor.

The crude reaction product obtained by the above fixed-bed continuous hydrogenation of the ester groups during the period between 5 hours and 10 hours after the start of the reaction was of the following composition.

| | |
|---|---|
| 1,4-Cyclohexanedimethanol | 97.8 wt. % |
| Dimethyl 1,4-cyclohexanedicarboxylate | 0.0 wt. % |
| Methyl 4-hydroxymethylcyclohexane-carboxylate | 0.0 wt. % |
| Low-boiling-point product | 2.2 wt. % |
| High-boiling-point product | Trace |

Example II-3

[First Reaction]

Following the general procedure of the first reaction of Example II-1, a solution consisting of:

| | |
|---|---|
| Dimethyl terephthalate | 50.0 wt. % |
| Dimethyl 1,4-cyclohexanedicarboxylate | 48.8 wt. % |
| Methyl 4-hydroxymethylcyclo-hexanecarboxylate | 0.3 wt. % |
| Methyl 4-methylcyclohexanecarboxylate | 0.9 wt. % | was fed to the top of the reactor at a rate of 200 L/h(F/V= 1.0/h), together with 192 Nm³/h of hydrogen gas (superficial linear velocity under the reaction conditions=6 cm/s), to continuously carry out ring hydrogenation at a pressure of 60 kgf/cm². The reaction temperature was adjusted to 133 to 139° C. in the upper part of the reactor, 133 to 137° C. in the middle part of the reactor and 131 to 135° C. in the lower part of the reactor. The maximum temperature difference in the reactor was 8° C.

The crude liquid reaction product obtained by the above fixed-bed continuous ring hydrogenation during the period between 5 hours and 15 hours after the start of the reaction was of the following composition.

| | |
|---|---|
| Dimethyl 1,4-cyclohexanedicarboxylate | 98.2 wt. % |
| Methyl 4-hydroxymethylcyclohexane-carboxylate | 0.4 wt. % |
| Methyl 4-methylcyclohexanecarboxylate | 1.4 wt. % |
| Dimethyl terephthalate | 0.0 wt. % |

[Second Reaction]

Following the general procedure of the second reaction in Example II-1, the crude product of the above first reaction was fed to the top of the reactor at a rate of 250 L/h(F/V= 2.46/h) at a pressure of 250 kgf/cm$^2$, together with 2567 Nm$^3$/h of hydrogen gas (superficial linear velocity under the reaction conditions=25 cm/s) to continuously carry out the hydrogenation of the ester groups. The reaction temperature was adjusted to 248 to 261° C. in the upper part of the reactor, 246 to 252° C. in the middle part of the reactor and 248 to 252° C. in the lower part of the reactor.

The reaction product obtained by the above fixed-bed continuous hydrogenation of the ester groups during the period between 5 hours and 10 hours after the start of the reaction was of the following composition.

| | |
|---|---|
| 1,4-Cyclohexanedimethanol | 97.8 wt. % |
| Dimethyl 1,4-cyclohexanedicarboxylate | 0.1 wt. % |
| Methyl 4-hydroxymethylcyclohexane-carboxylate | 0.3 wt. % |
| Low-boiling-point product | 1.8 wt. % |
| High-boiling-point product | Trace |

Example II-4

[Second Reaction]

The second reaction in Example II-1 was repeated with the exception that the crude product of the following composition obtained by continuing the first reaction of Example II-1 was used as the raw material and that a copper-chromite catalyst (51 wt. % of copper oxide and 49 wt. % of chromium oxide) was used. The catalyst was in the form of cylinders with a diameter of 3.5 mm and a height of 3.5 mm.

| | |
|---|---|
| Dimethyl 1,4-cyclohexanedicarboxylate | 97.8 wt. % |
| Methyl 4-hydroxymethylcyclohexane-carboxylate | 0.7 wt. % |
| Methyl 4-methylcyclohexanecarboxylate | 1.4 wt. % |
| Dimethyl terephthalate | 0.1 wt. % |

The crude product obtained by the above reaction during the period between 5 hours and 10 hours after the start of the reaction was of the following composition.

| | |
|---|---|
| 1,4-Cyclohexanedimethanol | 97.6 wt. % |
| Dimethyl 1,4-cyclohexanedicarboxylate | 0.0 wt. % |
| Methyl 4-hydroxymethylcyclohexane-carboxylate | 0.2 wt. % |
| Low-boiling-point product | 2.2 wt. % |
| High-boiling-point product | Trace |

Example II-5

[Second Reaction]

The second reaction in Example II-4 was repeated with the exception that a copper oxide/zinc oxide catalyst (41 wt. % of copper oxide, 50 wt. % of zinc oxide and 9 wt. % of aluminum oxide) was used. The catalyst was in the form of cylinders with a diameter of 3.5 mm and a height of 3.5 mm.

The crude product obtained by the above reaction during the period between 5 hours and 10 hours after the start of the reaction was of the following composition.

| | |
|---|---|
| 1,4-Cyclohexanedimethanol | 96.7 wt. % |
| Dimethyl 1,4-cyclohexanedicarboxylate | 0.4 wt. % |
| Methyl 4-hydroxymethylcyclohexane-carboxylate | 0.9 wt. % |
| Low-boiling-point product | 2.0 wt. % |
| High-boiling-point product | Trace |

Example II-6

[Second Reaction]

The second reaction in Example II-4 was repeated with the exception that a copper oxide/iron oxide catalyst (30 wt. % of copper oxide, 30 wt. % of iron oxide (FeO) and 40 wt. % of aluminum oxide as support) was used. The catalyst was in the form of cylinders with a diameter of 3.5 mm and a height of 3.5 mm.

The crude product obtained by the above reaction during the period between 5 hours and 10 hours after the start of the reaction was of the following composition.

| | |
|---|---|
| 1,4-Cyclohexanedimethanol | 94.2 wt. % |
| Dimethyl 1,4-cyclohexanedicarboxylate | 1.0 wt. % |
| Methyl 4-hydroxymethylcyclohexane-carboxylate | 2.2 wt. % |
| Low-boiling-point product | 2.5 wt. % |
| High-boiling-point product | 0.1 wt. % |

Example II-7

[Second Reaction]

The second reaction in Example II-4 was repeated with the exception that a copper oxide/aluminum oxide catalyst (60 wt. % of copper oxide, 6 wt. % of magnesium oxide and 34 wt. % of aluminum oxide as support) was used. The catalyst was in the form of cylinders with a diameter of 3.5 mm and a height of 3.5 mm.

The crude product obtained by the above reaction during the period between 5 hours and 10 hours after the start of the reaction was of the following composition.

| | |
|---|---|
| 1,4-Cyclohexanedimethanol | 93.6 wt. % |
| Dimethyl 1,4-cyclohexanedicarboxylate | 1.4 wt. % |
| Methyl 4-hydroxymethylcyclohexane-carboxylate | 3.0 wt. % |
| Low-boiling-point product | 1.9 wt. % |
| High-boiling-point product | 0.1 wt. % |

Example II-8

The influence of the length of the tubes in the reactor was determined in the following manner. The reaction was carried out under the same conditions as in Example II-1 with the exception that the feed rate of the raw material solution was doubled. Then, the obtained reaction product was fed again to the reactor under the same conditions. Thus, the reaction corresponding to the tube length of 10 m was carried out.

[First Reaction]
The first reaction in Example II-1 was repeated with the exception that a solution consisting of:

| | |
|---|---|
| Dimethyl terephthalate | 50.0 wt. % |
| Dimethyl 1,4-cyclohexanedicarboxylate | 48.5 wt. % |
| Methyl 4-hydroxymethylcyclohexane-carboxylate | 0.5 wt. % |
| Methyl 4-methylcyclohexanecarboxylate | 1.0 wt. % | was fed at a rate of 600 L/h(F/V=3.0/h), and the reaction was carried out for 5 hours. The obtained product was fed again at a rate of 600 L/h under the same conditions as in Example II-1 (F/V in total=1.5/h) to carry out the reaction.

The reaction product obtained by the above reaction during the period between 2 hours and 3 hours after the start of the reaction was of the following composition.

| | |
|---|---|
| Dimethyl 1,4-cyclohexanedicarboxylate | 97.5 wt. % |
| Methyl 4-hydroxymethylcyclohexane-carboxylate | 0.4 wt. % |
| Methyl 4-methylcyclohexanecarboxylate | 2.0 wt. % |
| Dimethyl terephthalate | 0.1 wt. % |

[Second Reaction]
The second reaction in Example II-1 was repeated with the exception that the above reaction product was used as the raw material and fed at twice the feed rate of Example II-1, i.e., at 378 L/h(F/V=3.68/h). The reaction was carried out for 5 hours. The product obtained by this reaction was fed again at a rate of 378 L/h(F/V in total=1.84/h) under the same conditions as in the second reaction in Example II-1.

The reaction product obtained by this reaction during the period between 2 hours and 3 hours after the start of the reaction was of the following composition.

| | |
|---|---|
| 1,4-Cyclohexanedimethanol | 97.6 wt. % |
| Dimethyl 1,4-cyclohexanedicarboxylate | 0.0 wt. % |
| Methyl 4-hydroxymethylcyclohexane-carboxylate | 0.1 wt. % |
| Low-boiling-point product | 2.2 wt. % |
| High-boiling-point product | Trace |

Example II-9
[First Reaction]
Ring hydrogenation was continuously carried out in the same manner as in Example II-2 with the exception that dimethyl isophthalate was used as the raw material in place of dimethyl terephthalate.

The obtained product was of the following composition.

| | |
|---|---|
| Dimethyl 1,3-cyclohexanedicarboxylate | 97.7wt.% |
| Methyl 3-hydroxymethylcyclohexane-carboxylate | 0.8wt.% |
| Methyl 3-methylcyclohexanecarboxylate | 1.5wt.% |
| Dimethyl isophthalate | 0.0wt.% |

[Second Reaction]
Ester reduction reaction was continuously carried out in the same manner as in Example II-2 with the exception that the above reaction product was used as the raw material.

The obtained reaction product was of the following composition.

| | |
|---|---|
| 1,3-Cyclohexanedimethanol | 97.3 wt. % |
| Dimethyl 1,3-cyclohexanedicarboxylate | 0.0 wt. % |
| Methyl 3-hydroxymethylcyclohexane-carboxylate | 0.1 wt. % |
| Low-boiling-point product | 2.6 wt. % |
| High-boiling-point product | Trace |

Example II-10
[First Reaction]
The first reaction in Example II-1 was repeated with the exception that a composition of the following make-up was used as the raw material and that the temperature difference in the tubes in the reactor was changed as described below.

| | |
|---|---|
| Dimethyl terephthalate | 50.0wt.% |
| Dimethyl 1,4-cyclohexanedicarboxylate | 48.9wt.% |
| Methyl 4-hydroxymethylcyclohexane-carboxylate | 0.4wt.% |
| Methyl 4-methylcyclohexanecarboxylate | 0.7wt.% |

The temperature of the reactor was adjusted to 175 to 180° C. in the upper part, 136 to 139° C. in the middle part and 118 to 125° C. in the lower part. The maximum temperature difference was 60° C.

The crude liquid product obtained by this fixed-bed continuous reaction during the period between 5 hours and 10 hours after the start of the reaction was of the following composition.

| | |
|---|---|
| Dimethyl 1,4-cyclohexanedicarboxylate | 86.0wt.% |
| Methyl 4-hydroxymethylcyclohexane-carboxylate | 1.2wt.% |
| Methyl 4-methylcyclohexanecarboxylate | 7.2wt.% |
| Dimethyl terephthalate | 5.6wt.% |

[Second Reaction]
The second reaction in Example II-1 was repeated with the exception that the crude liquid reaction product obtained above was used as the raw material. The reaction product obtained by this fixed-bed continuous ester group hydrogenation reaction during the period between 5 hours and 10 hours after the start of the reaction was of the following composition.
1,4-Cyclohexanedimethanol 84.7 wt. %

| | |
|---|---|
| 1,4-Cyclohexanedimethanol | 84.7 wt. % |
| Dimethyl 1,4-cyclohexanedicarboxylate | 0.0 wt. % |
| Methyl 4-hydroxymethylcyclohexane-carboxylate | 0.1 wt. % |
| Low-boiling-point product | 15.2 wt. % |
| High-boiling-point product | Trace |

Example II-11
[First Reaction]
The first reaction in Example II-1 was repeated with the exception that the concentration of dimethyl terephthalate in the raw material feed was decreased to 20 wt. %. Stated specifically, a solution consisting of:

| | |
|---|---|
| Dimethyl terephthalate | 20.0wt.% |
| Dimethyl 1,4-cyclohexanedicarboxylate | 78.2wt.% |
| Methyl 4-hydroxymethylcyclohexane-carboxylate | 0.5wt.% |
| Methyl 4-methylcyclohexanecarboxylate | 1.3wt.% | was fed to the top of the reactor at a rate of 750 L/h(F/V= 1.5/h), together with 207 Nm$^3$/h of hydrogen gas (superficial linear velocity under the reaction conditions=5 cm/s) to continuously carry out ring hydrogenation at a pressure of 80 kgf/cm$^2$. The temperature in the tubes was adjusted to 144 to 146° C. in the upper part of the reactor, 143 to 146° C. in the middle part of the reactor and 140 to 145° C. in the lower part of the reactor. The maximum temperature difference in the reactor was 6° C.

The crude liquid product obtained by this fixed-bed continuous ring hydrogenation reaction during the period between 5 hours and 10 hours after the start of the reaction was of the following composition.

| | |
|---|---|
| Dimethyl 1,4-cyclohexanedicarboxylate | 88.5wt.% |
| Methyl 4-hydroxymethylcyclohexane-carboxylate | 1.8wt.% |
| Methyl 4-methylcyclohexanecarboxylate | 2.1wt.% |
| Dimethyl terephthalate | 7.6wt.% |

[Second Reaction]

The second reaction in Example II-1 was repeated with the exception that the above crude liquid product was used as the raw material. The reaction product obtained by this fixed-bed continuous hydrogenation of the ester groups during the period between 5 hours and 10 hours after the start of the reaction was of the following composition.

| | |
|---|---|
| 1,4-Cyclohexanedimethanol | 88.9 wt. % |
| Dimethyl 1,4-cyclohexanedicarboxylate | 0.0 wt. % |
| Methyl 4-hydroxymethylcyclohexane-carboxylate | 0.1 wt. % |
| Low-boiling-point product | 11.0 wt. % |
| High-boiling-point product | Trace |

Comparative Example II-2
[Second Reaction]

The second reaction in Example II-2 was repeated with the exception that the same raw material as used in Example II-4 (crude reaction product obtained by continuing the first reaction of Example II-1) was employed and that the reaction pressure was changed to 170 kgf/cm$^2$.

The crude product obtained by this reaction during the period between 5 hours and 10 hours after the start of the reaction was of the following composition.

| | |
|---|---|
| 1,4-Cyclohexanedimethanol | 84.1wt.% |
| Dimethyl 1,4-cyclohexane-dicarboxylate | 0.0wt.% |
| Methyl 4-hydroxymethylcyclohexane-carboxylate | 9.2wt.% |
| Low-boiling-point product | 2.2wt.% |
| High-boiling-point product | 4.5wt.% |

Comparative Example II-3
[Second Reaction]

The second reaction in Example II-2 was repeated with the exception that the same raw material as used in Example II-4 was employed and that the hydrogen gas superficial linear velocity was changed to 3 cm/s.

The crude product obtained during the period between 5 hours and 10 hours after the start of the reaction was of the following composition.

| | |
|---|---|
| 1,4-Cyclohexanedimethanol | 87.8wt.% |
| Dimethyl 1,4-cyclohexanedicarboxylate | 1.0wt.% |
| Methyl 4-hydroxymethylcyclohexane-carboxylate | 5.8wt.% |
| Low-boiling-point product | 2.2wt.% |
| High-boiling-point product | 3.2wt.% |

Comparative Example II-4
[First Reaction]

The first reaction in Example II-1 was repeated with the exception that the raw material feed was fed at four times the feed rate in Example II-1. The procedure of feeding the obtained product to the reactor under the same conditions was repeated three times. Thus, the reaction corresponding to the tube length of 20 m was carried out. Stated specifically, a solution consisting of:

| | |
|---|---|
| Dimethyl terephthalate | 50.0wt.% |
| Dimethyl 1,4-cyclohexanedicarboxylate | 48.9wt.% |
| Methyl 4-hydroxymethylcyclohexane-carboxylate | 0.3wt.% |
| Methyl 4-methylcyclohexanecarboxylate | 0.8wt.% | was fed at a rate of 1200 L/h(F/V=6.0/h), and the reaction was carried out for about 5 hours under the same condition as in Example II-1. The obtained product was fed again to the reactor at a rate of 1200 L/h under the same conditions as in Example II-1. The procedure of feeding the obtained product to the reactor under the same conditions was repeated.

The reaction product obtained in the fourth reaction of the above procedure (F/V in total=1.5/h) during the period between 2 hours and 3 hours after the start of the reaction was of the following composition.

| | |
|---|---|
| Dimethyl 1,4-cyclohexanedicarboxylate | 89.4wt.% |
| Methyl 4-hydroxymethylcyclohexane-carboxylate | 0.8wt.% |
| Methyl 4-methylcyclohexanecarboxylate | 3.5wt.% |
| Dimethyl terephthalate | 6.3wt.% |

[Second Reaction]

The second reaction was carried out in the same manner as in the first reaction to effect the reaction corresponding to the tube length of 20 m. Thus, the reaction was carried out for 5 hours using the same raw material as used in Example II-4 under the same conditions as in the second reaction of Example II-1 with the exception that the raw material was fed at four times the feed rate in Example II-1, i.e., at 752 L/h (F/V=7.35/h). The obtained reaction product was fed again to the reactor at a rate of 752 L/h under the same conditions as in the second reaction of Example II-1. The procedure of feeding the obtained product to the reactor under the same conditions was repeated three times.

The reaction product obtained in the fourth reaction of the above procedure (F/V in total=1.84/h) during the period between 2 hours and 3 hours after the start of the reaction was of the following composition.

| | |
|---|---|
| 1,4-Cyclohexanedimethanol | 84.8wt.% |
| Dimethyl 1,4-cyclohexanedicarboxylate | 3.5wt.% |
| Methyl 4-hydroxymethylcyclohexane-carboxylate | 7.8wt.% |
| Low boiling-point product | 1.8wt.% |
| High-boiling-point product | 2.1wt.% |

Comparative Example II-1

The reactor used was a pressure-resistant column reactor with an inner diameter of 159 mm and a length of 2 m, which comprises a shell for heating and cooling by a heat transfer medium. The raw material and hydrogen fed to the top of the reactor pass through perforated plate provided in the upper part of the reactor and are distributed through the zone to be charged with a catalyst.

[First Reaction]

The reactor was packed with 35 L of tableted catalyst (3.2 mm in diameter and 3.2 mm in height) comprising 1.0 wt. % of Ru supported on alumina. To the top of the reactor, a solution consisting of:

| | |
|---|---|
| Dimethyl terephthalate | 50.0wt.% |
| Dimethyl 1,4-cyclohexanedicarboxylate | 48.5wt.% |
| Methyl 4-methylcyclohexanecarboxylate | 1.0wt.% |
| Methyl 4-hydroxymethylcyclohexane-carboxylate | 0.5wt.% | was fed at a rate of 105 L/h(F/V=1.5/h), together with 182 Nm³/h of hydrogen gas (superficial linear velocity under the reaction conditions=5 cm/s), to continuously carry out ring hydrogenation at a pressure of 80 kgf/cm². The reaction temperature was measured with a thermometer set in the central part of the reactor, and found to be 144 to 178° C.

The crude reaction product obtained by the above fixed-bed continuous ring hydrogenation during the period between 3 hours and 5 hours after the start of the reaction was of the following composition.

| | |
|---|---|
| Dimethyl 1,4-cyclohexanedicarboxylate | 79.9wt.% |
| Methyl 4-hydroxymethylcyclohexane-carboxylate | 3.2wt.% |
| Methyl 4-methylcyclohexanecarboxylate | 7.5wt.% |
| Dimethyl terephthalate | 2.6wt.% |
| Low-boiling-point product | 6.8wt.% |

[Second Reaction]

The reactor of the same type as in the above first reaction was charged with 35 L of tableted copper-chromite catalyst (3.5 mm in diameter and 3.5 mm in height) containing barium and manganese (47 wt. % of copper oxide, 48 wt. % of chromium oxide, 2.5 wt. % of barium oxide and 2.5 wt. % of manganese oxide). The catalyst was then subjected to preliminary activation treatment under the same conditions as in Example II-1. After the preliminary activation treatment, the raw material of the same composition as in Example II-4 was fed to the top of the reactor at a rate of 66 L/h(F/V=1.84/h) and a pressure of 250 kgf/cm², together with 1916 Nm³/h of hydrogen gas (superficial linear velocity under the reaction conditions=20 cm/s), to continuously carry out hydrogenation of ester groups at 230 to 245° C.

The reaction product obtained by the above reaction during the period between 5 hours and 6 hours after the start of the reaction was of the following composition.

| | |
|---|---|
| 1,4-Cyclohexanedimethanol | 75.7wt.% |
| Dimethyl 1,4-cyclohexanedicarboxylate | 5.8wt.% |
| Methyl 4-hydroxymethylcyclohexane-carboxylate | 11.5wt.% |
| Low-boiling-point product | 2.8wt.% |
| High-boiling-point product | 4.2wt.% |

The embodiment II of the present invention provides a production process which is capable of remarkably improving the productivity per reactor and giving high-quality cyclohexanedimethanol by a simplified procedure in a high yield on a commercial scale.

The following are examples of embodiment III.

[Reactor]

The reactor used in the following examples was a pressure-resistant vessel with an internal diameter of 30 mm, a length of 3 m and an internal volume of 2100 ml. The temperature of the reactor was adjustable by heating or cooling with a heat transfer medium. The reaction temperature was measured with a multi-point thermometer provided in the reactor.

[Composition Analysis]

The compositions of the ester as the raw material and the reaction products in the following examples were analyzed by gas chromatography.

Example III-1

The reactor was packed with 2.8 kg of tableted copper-chromite catalyst (3.5 mm in diameter and 3.5 mm in height) containing barium and manganese (46 wt. % of copper oxide, 49 wt. % of chromium oxide, 2.4 wt. % of barium oxide and 2.6 wt. % of manganese oxide). The catalyst was then subjected to a preliminary activation treatment in a stream of hydrogen-nitrogen mixed gas at atmospheric pressure and at a temperature of 150 to 200° C. while gradually increasing the hydrogen concentration.

After the preliminary activation treatment, 2.7 kg/h of dimethyl 1,4-cyclohexanedicarboxylate with a purity of 99.5% (containing 0.5% of methyl 4-hydroxymethylcyclohexanecarboxylate) and 270 g/h of methanol (10 wt. % relative to the starting ester) were fed to the top of the reactor at a hydrogen pressure of 200 kgf/cm², together with 27 Nm³/h of hydrogen gas (superficial linear velocity under the reaction conditions=10 cm/s). Thus, hydrogenation of the ester groups was continuously carried out.

The reaction temperature was adjusted to 236 to 240° C. in the upper part of the reactor, 239 to 241° C. in the middle part of the reactor and 237 to 238° C. in the lower part of the reactor. The reaction product obtained by this fixed-bed continuous hydrogenation reaction during the period between 5 hours and 10 hours after the start of the reaction was of the following composition.

| | |
|---|---|
| 1,4-Cyclohexanedimethanol | 95.2 wt. % |
| Dimethyl 1,4-cyclohexanedicarboxylate | Trace |

-continued

| | |
|---|---|
| Methyl 4-hydroxymethylcyclohexane-carboxylate | 0.3 wt. % |
| Low-boiling-point product | 2.1 wt. % |
| High-boiling-point product | 2.4 wt. % |

Example III-2

Hydrogenation of ester groups was continuously carried out in the same manner as in Example III-1 with the exception that methanol was fed at a rate of 810 g/h(30 wt. % relative to the starting ester). The reaction product obtained by the fixed-bed continuous hydrogenation during the period between 5 hours and 10 hours after the start of the reaction was of the following composition.

| | |
|---|---|
| 1,4-Cyclohexanedimethanol | 97.4wt.% |
| Dimethyl 1,4-cyclohexanedicarboxylate | 0.0wt.% |
| Methyl 4-hydroxydimethylcyclohexane-carboxylate | 0.1wt.% |
| Low-boiling-point product | 1.5wt.% |
| High-boiling-point product | 1.0wt.% |

Example III-3

Hydrogenation of ester groups was continuously carried out in the same manner as in Example III-2 with the exception that the reaction temperature was adjusted to 228 to 230° C. in the upper part of the reactor, 229 to 231° C. in the middle part of the reactor and 227 to 229° C. in the lower part of the reactor. The reaction product obtained by the fixed-bed continuous hydrogenation reaction during the period between 5 hours and 10 hours after the start of the reaction was of the following composition.

| | |
|---|---|
| 1,4-Cyclohexanedimethanol | 97.5wt.% |
| Dimethyl 1,4-cyclohexanedicarboxylate | 0.0wt.% |
| Methyl 4-hydroxymethylcyclohexane-carboxylate | 0.4wt.% |
| Low-boiling-point product | 0.9wt.% |
| High-boiling-point product | 1.2wt.% |

Example III-4

Hydrogenation of ester groups was continuously carried out in the same manner as in Example III-1 with the exception that methanol was fed at a rate of 2160 g/h(80 wt. % relative to the starting ester). The reaction product obtained by the fixed-bed continuous hydrogenation reaction during the period between 5 hours and 10 hours after the start of the reaction was of the following composition.

| | |
|---|---|
| 1,4-Cyclohexanedimethanol | 98.9wt.% |
| Dimethyl 1,4-cyclohexanedicarboxylate | 0.0wt.% |
| Methyl 4-hydroxymethylcyclohexane-carboxylate | 0.1wt.% |
| Low-boiling-point product | 0.7wt.% |
| High-boiling-point product | 0.3wt.% |

Example III-5

Hydrogenation of ester groups was continuously carried out in the same manner as in Example III-1 with the exception that methanol was fed at a rate of 2700 g/h (100 wt. % relative to the starting ester). The reaction product obtained by the fixed-bed continuous hydrogenation reaction during the period between 5 hours and 10 hours after the start of the reaction was of the following composition.

| | |
|---|---|
| 1,4-Cyclohexanedimethanol | 98.7wt.% |
| Dimethyl 1,4-cyclohexanedicarboxylate | 0.0wt.% |
| Methyl 4-hydroxymethylcyclohexane-carboxylate | 0.2wt.% |
| Low-boiling-point product | 0.7wt.% |
| High-boiling-point product | 0.4wt.% |

Example III-6

Hydrogenation of ester groups was continuously carried out in the same manner as in Example III-1 with the exception that methanol was not used. The reaction product obtained by the fixed-bed continuous hydrogenation reaction during the period between 5 hours and 10 hours after the start of the reaction was of the following composition.

| | |
|---|---|
| 1,4-Cyclohexanedimethanol | 86.2wt.% |
| Dimethyl 1,4-cyclohexanedicarboxylate | 0.5wt.% |
| Methyl 4-hydroxymethylcyclohexane-carboxylate | 2.2wt.% |
| Low-boiling-point product | 5.1wt.% |
| High-boiling-point product | 6.0wt.% |

In this Example III-6, no alcohol was used so that the yield of 1,4-cyclohexanedimethanol is lower than those of Examples III-1 to III-5.

In Example II-1 according to embodiment II, the multitubular reactor (comprising 15 tubes having a diameter of 43 mm and a length of 5 m) so that the high yield can be achieved even without use of the alcohol. However, when a single-column reactor having a relatively short length of 3 m as in the above Example III-6, the residence time within the reactor is short and therefore there is a tendency that the yield becomes lowered.

The production process according to embodiment III of the present invention is a process wherein low-boiling-point and high-boiling-point products are produced in reduced amounts by using a simple apparatus, namely without using a complicated reactor such as a multitubular reactor. Further, alicyclic alcohols, in particular cyclohexanedimethanol, can be produced in high yields. Therefore, the process of the present invention is very advantageous for the commercial purpose.

The present invention will be described below in detail with reference to examples of embodiment IV, wherein the characteristics of the catalysts were tested and evaluated in the following manners.

Chlorine content (%): Measured by titrimetric method using silver nitrate. The end point for the titration was determined by checking excess silver nitrate with an indicator (potassium chromate) for the color change point (from yellow to faint red).

Dispersion: Determined by the gas adsorption method.

Surface distribution (%): Determined with an X-ray microanalyzer (EPMA).

Pore volume: Determined with a mercury intrusion porosimetry.

The catalysts used in the following examples were tableted catalyst (3.2 mm in diameter and 3.2 mm in height) comprising 0.5 wt. % of Ru supported on alumina.

Example IV-1

A fixed-bed continuous reactor (20 mm in inner diameter, 5 m in length and 1.57 liters in volume) was used, in which three parts thereof, namely the upper, middle and lower parts thereof, can be independently heated or cooled with respective electric heaters or cooling fans. The reactor was charged with 1.83 kg of tableted catalyst (3.2 mm in diameter and 3.2 mm in height) comprising 0.5 wt. % of Ru supported on alumina, the catalyst having the characteristics shown in Table 2.

To the top of the reactor, a raw material solution consisting of:

| | |
|---|---|
| Dimethyl terephthalate (hereinafter "DMT") | 50 wt. % |
| Dimethyl 1,4-cyclohexanedicarboxylate (hereinafter "HDMT") | 48.7 wt. % |
| Methyl 4-hydroxymethylcyclohexane-carboxylate (hereinafter "MOL") | 0.3 wt. % |
| Methyl 4-methylcyclohexanecarboxylate (hereinafter "MME") | 1.0 wt. % | was fed at a rate of 3.7 L/h(F/V=1.18/h), together with 1.46 Nm$^3$/h of hydrogen gas (superficial linear velocity under the reaction conditions=4 cm/s), to continuously carry out ring hydrogenation at a pressure of 50 kgf/cm$^2$.

The reaction temperature was 144 to 148° C. in the upper part of the reactor, 143 to 146° C. in the middle part of the reactor and 140 to 145° C. in the lower part of the reactor. The fixed-bed continuous ring hydrogenation was carried out for 10 hours, and composition of the obtained crude reaction product was analyzed by gas chromatography. The results are shown in Table 2.

Example IV-2

The reactor of the same type as in Example IV-1 was charged with 1.85 kg of preformed Ru-supported catalyst having the characteristics shown in Table 2. The raw material solution described in Example IV-1 was fed to the top of the reactor at a rate of 2.7 L/h (F/V=0.86/h), together with 2.85 Nm$^3$/h of hydrogen gas (superficial linear velocity under the reaction conditions=6 cm/s), to continuously carry out ring hydrogenation at a pressure of 65 kgf/cm$^2$.

The reaction temperature was 152 to 154° C. in the upper part of the reactor, 145 to 149 ° C. in the middle part of the reactor and 143 to 147° C. in the lower part of the reactor. The fixed-bed continuous ring hydrogenation was carried out for 10 hours, and the composition of the obtained crude reaction product was analyzed by gas chromatography. The results are shown in Table 2.

Example IV-3

Ring hydrogenation was carried out in the same manner as in Example IV-2 with the exception of using 1.79 kg of tableted supported Ru catalyst having the characteristics shown in Table 2. The reaction temperature was 151 to 155° C. in the upper part of the reactor, 145 to 151° C. in the middle part of the reactor and 143 to 149° C. in the lower part of the reactor. The fixed-bed continuous ring hydrogenation was carried out for 10 hours, and the composition of the obtained reaction product was analyzed by gas chromatography. The results are shown in Table 2.

Example IV-4

Ring hydrogenation was carried out in the same manner as in Example IV-2 with the exception of using 1.86 kg of tableted supported Ru catalyst with the characteristics shown in Table 2. The reaction temperature was 152 to 155° C. in the upper part of the reactor, 146 to 151° C. in the middle part of the reactor and 144 to 149° C. in the lower part of the reactor. The fixed-bed continuous ring hydrogenation was carried out for 10 hours, and the composition of the obtained crude reaction product was analyzed by gas chromatography. The results are shown in Table 2.

Example IV-5

Ring hydrogenation was carried out in the same manner as in Example IV-2 with the exception of using 1.88 kg of tableted supported Ru catalyst with the characteristics shown in Table 2. The reaction temperature was 152 to 155° C. in the upper part of the reactor, 146 to 150° C. in the middle part of the reactor and 144 to 149° C. in the lower part of the reactor. The fixed-bed continuous ring hydrogenation was carried out for 10 hours, and the composition of the obtained crude reaction product was analyzed by gas chromatography. The results are shown in Table 2.

Comparative Example IV-1

Ring hydrogenation was carried out in the same manner as in Example IV-2 with the exception of using 1.83 kg of tableted supported Ru catalyst with the characteristics shown in Table 2. The reaction temperature was 152 to 153° C. in the upper part of the reactor, 146 to 150° C. in the middle part of the reactor and 144 to 148° C. in the lower part of the reactor. The above fixed-bed continuous ring hydrogenation was carried out for 10 hours, and the composition of the obtained crude reaction product was analyzed by gas chromatography. The results are shown in Table 2.

Example IV-6

Ring hydrogenation was carried out in the same manner as in Example IV-2 with the exception that tableted supported Ru catalyst (chlorine content of 205 ppm, dispersion of 22%, surface distribution of 90 wt. % and pore volume of 0.33 cc/g) was used in an amount of 1.76 kg and that a solution consisting of:

| | |
|---|---|
| Dimethyl isophthalate | 50.0wt.% |
| Dimethyl 1,3-cyclohexanedicarboxylate | 48.2wt.% |
| Methyl 3-hydroxymethylcyclohexane-carboxylate | 0.5wt.% |
| Methyl 3-methylcyclohexanecarboxylate | 1.3wt.% | was used as the raw material. The reaction temperature was 150 to 153° C. in the upper part of the reactor, 146 to 148° C. in the middle part of the reactor and 144 to 147° C. in the lower part of the reactor. The fixed-bed continuous ring hydrogenation was carried out for 10 hours, and the composition of the obtained crude reaction product was analyzed by gas chromatography. The results are shown below.

| | |
|---|---|
| Dimethyl 1,3-cyclohexanedicarboxylate | 97.9wt.% |
| Methyl 3-hydroxymethylcyclohexane-carboxylate | 0.7wt.% |

| -continued | |
|---|---|
| Methyl 3-methylcyclohexanecarboxylate | 1.3wt.% |
| Dimethyl isophthalate | 0.1wt.% |

TABLE 2

| | Example | | | | | Comp. Ex. |
|---|---|---|---|---|---|---|
| | IV-1 | IV-2 | IV-3 | IV-4 | IV-5 | IV-1 |
| Characteristics of catalyst | | | | | | |
| Chlorine content (ppm) | 230 | 180 | 230 | 220 | 230 | 670 |
| Dispersion (%) | 25 | 31 | 11 | 25 | 20 | 25 |
| Surface distribution (wt %) | 89 | 94 | 85 | 71 | 81 | 92 |
| Pore volume (cc/g) | 0.30 | 0.35 | 0.31 | 0.33 | 0.15 | 0.32 |
| Reaction product composition (wt. %) | | | | | | |
| HDMT | 97.9 | 98.1 | 95.5 | 95.4 | 94.2 | 92.3 |
| DMT | 0.1 | 0.2 | 1.8 | 2.2 | 2.2 | 0.3 |
| MOL | 0.6 | 0.4 | 1.2 | 1.1 | 1.4 | 2.4 |
| MME | 1.4 | 1.3 | 1.5 | 1.3 | 2.2 | 5.0 |

Embodiment IV of the present invention provides a simple and commercially advantageous process for producing cyclohexanedicarboxylic acid dialkyl esters using a special preformed supported Ru catalyst, the process being capable of giving high-quality cyclohexane-dicarboxylic acid dialkyl ester in a high yield with remarkably improved productivity and safety.

Therefore, when a cyclohexanedicarboxylic acid dialkyl ester is prepared by such a method, the use of such cyclohexanedicarboxylic acid dialkyl ester as a raw material can advantageously give the desired cyclohexanedimethanol.

What is claimed is:

1. A process for preparing cyclohexanedimethanol represented by the formula (1):

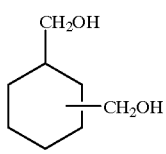
(1)

the process comprising the steps of
(a) ring hydrogenating aromatic dicarboxylic acid dialkyl ester represented by the formula (3)

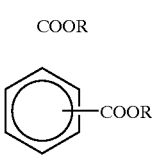
(3)

(wherein R is an alkyl group having 1 to 4 carbon atoms), in the presence of a preformed supported ruthenium catalyst by a fixed-bed continuous reaction to give a cyclohexanedicarboxylic acid dialkyl ester represented by the formula (2):

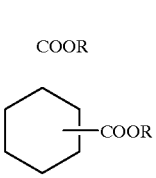
(2)

(wherein R is as defined above), and
(b) hydrogenating the cyclohexanedicarboxylic acid dialkyl ester obtained in the step (a) and represented by the formula (2) by a fixed-bed continuous reaction in the presence of a preformed copper-containing catalyst under the conditions of reaction temperature of 225 to 280° C., hydrogen pressure of 200 to 250 kgf/cm$^2$ and hydrogen gas feed rate of 2 to 20 cm/s in terms of superficial linear velocity and the feed rate of the cyclohezanedicarboxylic acid dialkyl ester per hour per unit volume of the catalyst bed in the reactor of 0.2 to 2.0/h., wherein both of step (a) and step (b) are of a single column type reactor.

2. The process for preparing cyclohexanedimethanol according to claim 1, wherein
the cyclohexanedimethanol of the formula (1) is 1,4-cyclohexanedimethanol;
the aromatic dicarboxylic acid dialkyl ester of the formula (3) is terephthalic acid dialkyl ester;
the cyclohexanedicarboxylic acid dialkyl ester of the formula (2) is 1,4-cyclohexanedicarboxylic acid dialkyl ester; and
the preformed copper-containing catalyst is a preformed copper chromite catalyst.

3. The process for preparing cyclohexanedimethanol according to claim 2, wherein the terephthalic acid dialkyl ester is dimethyl terephthalate.

4. The process for preparing cyclohexanedimethanol represented by the formula (1):

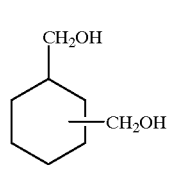
(1)

the process comprising the steps of
(a) continuously feeding the aromatic dicarboxylic acid dialkyl ester and hydrogen to the top of a multitubular pressure-resistant reactor packed with the preformed supported ruthenium catalyst to effect hydrogenation under a gas-liquid mixed phase condition, and removing excess hydrogen and the corresponding cyclohexanedicarboxylic acid dialkyl ester from the bottom of said reactor, wherein each tube of the multitubular reactor has an inner diameter of 2.5 to 10 cm and a length of 3 to 15 m, and
(b) continuously feeding the cyclohexanedicarboxylic acid dialkyl ester obtained in step (a) above and hydrogen to the top of a multitubular pressure-resistant reactor packed with the preformed copper-containing catalyst to effect hydrogenation under a gas-liquid mixed phase condition, wherein reaction temperature is 200 to 280° C., hydrogen pressure is 185 to 300 kgf/cm² and hydrogen gas feed rate is 5 to 30 cm/s in terms of superficial linear velocity, and removing excess hydrogen and the resulting cyclohexanedimethanol from the bottom of said reactor, wherein each tube of the multitubular reactor has an inner diameter of 2.5 to 10 cm and a length of 3 to 5 m, wherein the number of tubes is 10 to 2000 in both of step (a) and step (b).

5. The process for preparing cyclohexanedimethanol according to claim 4, wherein in step (a), the aromatic dicarboxylic acid dialkyl ester is dimethyl terephthalate, dimethyl isophthalate or dimethyl phthalate.

6. The process for preparing cyclohexanedimethnaol according to claim 4, wherein in step (a), the aromatic dicarboxylic acid dialkyl ester is fed as it is, or fed as admixed with a reaction product of step (a) predominantly comprising the cyclohexanedicarboxylic acid dialkyl ester; and wherein the hydrogenation in step (a) is carried out at a reaction temperature of 120 to 180° C., hydrogen pressure of 30 to 100 kgf/cm² and hydrogen gas feed rate of 1 to 15 cm/s in terms of superficial linear velocity.

7. The process for preparing cyclohexanedimethanol according to claim 6, wherein the aromatic dicarboxylic acid dialkyl ester is fed as admixed with the reaction product of step (a), and the concentration of the aromatic dicarboxylic acid dialkyl ester in the mixture is at least 30% by weight.

8. The process for preparing cyclohexanedimethnaol according to claim 4, wherein in step (b), the cyclohexanedicarboxylic acid dialkyl ester is fed as it is, or fed as admixed with a reaction product of step (b) predominantly comprising the cyclohexanedimethnaol, the concentration of the cyclohexanedicarboxylic acid dialkyl ester in the mixture being at least 90 weight %, and wherein the hydrogenation in step (b) is carried out under the conditions of reaction temperature of 200 to 280° C., hydrogen pressure of 185 to 300 kgf/cm² and hydrogen gas feed rate of 5 to 30 cm/s in terms of superficial linear velocity.

9. The process for preparing cyclohexanedimethanol according to claim 4, wherein in step (b), the feed rate of the cyclohexanedicarboxylic acid dialkyl ester per hour per unit volume of the catalyst bed in the multitubular pressure-resistant reactor is 1.1 to 3.0/h.

10. The process for preparing cyclohexanedimethanol according to claim 4, wherein the hydrogenation in step (a) is carried out while controlling the temperature difference within the multitubular reactor to not greater than 50° C.

11. The process for preparing cyclohexanedimethanol according to claim 4, wherein the multitubular reactor used in step (a) comprises a shell and a plurality of tubes contained in the shell, wherein the shell is divided into at least two separate zones, through each of which a heat transfer medium is circulated for heating or cooling the tubes, each of the heat transfer media being independently heated or cooled in such a manner that the temperature difference within the reactor is controlled to not greater than 50° C.

12. The process for preparing cyclohexandimethanol represented by the formula (1):

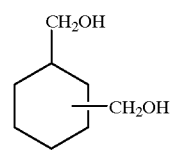

(1)

the process comprising the steps of
(a) ring hydrogenating aromatic dicarboxylic acid dialkyl ester represented by the formula (3)

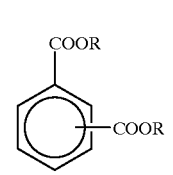

(3)

(wherein R is an alkyl group having 1 to 4 carbon atoms) in the presence of a preformed supported ruthenium catalyst by a fixed-bed continuous reaction to give a cyclohexanedicarboxylic acid dialkyl ester represented by the formula (2):

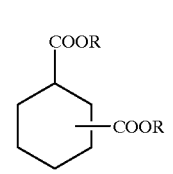

(2)

(wherein R is as defined above), and
(b) hydrogenating the cyclohexanedicarboxylic acid dialkyl ester obtained in the step (a) and represented by the formula (2) by a fixed-bed continuous reaction in the presence of preformed copper-chromite catalyst under the conditions of reaction temperature of 200 to 280° C., hydrogen pressure of 185 to 300 kgf/cm² and hydrogen gas feed rate of 5 to 30 cm/s in terms of superficial linear velocity, wherein in step (b), hydrogen, the cyclohexanedicarboxylic acid dialkyl ester and an aliphatic alcohol having 1 to 4 carbon atoms and an aliphatic alcohol having 1 to 4 carbon atoms are continuously fed to the top of a reactor packed with the preformed copper-containing catalyst in an amount of 10 to 80% by weight based on the cyclohexanedicarboxylic acid dialkyl ester to carry out hydrogenation under a gas-liquid mixed phase condition, and excess hydrogen, the reaction product and the aliphatic alcohol having 1 to 4 carbon atoms are removed from the bottom of the reactor.

* * * * *

UNITED STATES PATENT AND TRADEMARK OFFICE
CERTIFICATE OF CORRECTION

PATENT NO. : 6,187,968 B1
DATED : February 13, 2001
INVENTOR(S) : Itoh

It is certified that error appears in the above-identified patent and that said Letters Patent is hereby corrected as shown below:

Column 45,
Line 10, "5" should read -- 15 --.

Signed and Sealed this

Eighteenth Day of June, 2002

Attest:

JAMES E. ROGAN
Attesting Officer   Director of the United States Patent and Trademark Office